US006537567B1

(12) United States Patent
Niklason et al.

(10) Patent No.: US 6,537,567 B1
(45) Date of Patent: Mar. 25, 2003

(54) TISSUE-ENGINEERED TUBULAR CONSTRUCT HAVING CIRCUMFERENTIALLY ORIENTED SMOOTH MUSCLE CELLS

(75) Inventors: Laura E. Niklason, Hillsborough, MA (US); Jinming Gao, Shaker Hts, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/109,427

(22) Filed: Jul. 2, 1998

Related U.S. Application Data
(60) Provisional application No. 60/052,553, filed on Jul. 15, 1997, and provisional application No. 60/051,634, filed on Jul. 3, 1997.

(51) Int. Cl.$^7$ .............................. A61F 2/00; A61F 13/00; A61K 35/34; A01N 63/00; A01N 65/00
(52) U.S. Cl. ...................... 424/423; 424/93.7; 424/422; 424/548; 424/569; 424/572; 435/325; 435/363; 435/366; 435/377; 435/395
(58) Field of Search .............................. 435/287.1, 366, 435/371, 325, 363, 377, 395; 424/395, 422, 93.7, 423, 548, 569, 572

(56) References Cited

U.S. PATENT DOCUMENTS

| | | | |
|---|---|---|---|
| 5,618,718 A | 4/1997 | Auger et al. | 435/366 |
| 5,792,603 A | 8/1998 | Dunkelman et al. | 435/1.2 |
| 5,846,828 A | 12/1998 | Peterson et al. | 435/399 |
| 5,863,531 A | 1/1999 | Naughton et al. | 424/93.7 |

FOREIGN PATENT DOCUMENTS

| | | |
|---|---|---|
| EP | 0 408 378 A2 | 1/1991 |
| EP | 6 408 378 | 1/1991 |
| WO | WO94/25584 | 11/1994 |
| WO | 94 25584 | 11/1994 |
| WO | WO96/21003 | 7/1996 |
| WO | 96 21003 | 7/1996 |
| WO | WO96/34090 | 10/1996 |
| WO | 96 34090 | 10/1996 |

OTHER PUBLICATIONS

Barera et al, *J. Am. Chem. Soc.*, 115:11010–11011 (1993).
Bell, *J. Cellular Biochem.*, 56:147–149 (1994).
Cao et al., *Transplantation Proc.*, 26(6):3390–3391 (1994).
Chen et al., *Circulation*, 89:1922–1928 (1994).
Cima et al., *Biotechnol. and Bioeng.*, 38:145–158 (1991).
Cima et al., *Chem. Eng. Prog.*, 46–53 (1993).
Connolly et al., *Trans. ASAIO*, 34:1043–1046 (1988).
D'Amore et al., *Growth Factors*, 8:61–75 (1993).
Edelman et al., *Biomaterials*, 12:619–626 (1991).
Freed et al., *J. Cell. Biochem.*, 51:257–264 (1993).
Freed et al., *J. Biomed. Mat. Res.*, 28:891–899 (1994).
Freed et al., *Bio/Technology*, 12:689–693 (1994).
Gilbert et al., *Transplantation*, 56(2):423–427 (1993).
Gilding et al., *Polymer*, 20:1459–1464 (1979).
Greisler et al., *Circulation*, 78(Suppl. I):16–112 (1988).
Jarrell et al., *ASAIO Trans.*, 113:120–122 (1991).
Langer et al., *Science*, 260:920–926 (1993).
Massia et al., *Ann. N.Y. Acad. Sci.*, 589:261–270 (1990).
Mazzucotelli et al., *Artificial Organs*, 17(9):787–790 (1993).
Mooney et al., *Mat. Res. Soc. Symp. Proc.*, 252:345–352 (1992).
Mooney et al., *Cell Transplantation*, 3(2):203–210 (1994).
Mooney et al., *Transplantation Proc.*, 26(6):3425–3426 (1994).
Niklason et al., *Transplant Immunology*, 5:303–306 (1997).
Ott et al., *Surgery*, 117:334–339 (1995).
Rogelj et al., *J. Cell Biol.*, 109:823–831 (1989).
Shayani et al., *J. Surg. Res.*, 57:495–504 (1994).
Takeda et al., *Transplantation Proc.*, 27(1):635–636 (1995).
Vacanti et al., *Transplantation Proc.*, 26(6):3434–3435 (1994).
Weinberg et al., *Science*, 231:397–400 (1986).
Wintermantel et al., *ASAIO Trans.*, 37:M334–M336 (1991).
Greisler et al., *Biomaterials*, 17:329–336 (1996).
Hirai et al., *Cell Transplantation*, 4(6):597–608 (1995).
L'Heureux et al., *The FASEB Journal*, 12:47–56 (1998).
L'Heureux et al., *Jour. of Vascular Surgery*, 17:499–509 (1993).

(List continued on next page.)

*Primary Examiner*—David M. Naff
*Assistant Examiner*—Deborah K. Ware
(74) *Attorney, Agent, or Firm*—Choate, Hall & Stewart

(57) ABSTRACT

Improved methods for the production of tissue-engineered constructs, including muscular tissue constructs such as vascular constructs, are disclosed. The methods include the use of improved substrates for cell growth, improved cell culture media for cell growth, and the use of distensible bodies to impart pulsatile stretching force to lumens of constructs during growth. Also disclosed are improved products and methods for making those products, including substrates and cell culture media, for tissue engineering and tissue culture generally. Improved muscular tissue constructs, including vascular constructs, are also disclosed, which may be used in medicine for the repair or replacement of damaged natural structures. In an embodiment, a muscular, tubular tissue-engineered construct is prepared having a wall of mammalian smooth muscle cells oriented circumferentially about a lumen of the construct at a cell density of at least $10^7$ cells/cc.

9 Claims, 2 Drawing Sheets

OTHER PUBLICATIONS

Ziegler et al., *Annals of Biomedical Engineering*, 23:216–225 (1995).

Mooney et al., *Biomaterials*, 17(2):115–124 (1996).

Kanda et al., *Cell Transplantation*, 2(6):475–484 (1993).

Kanda K and Matsuda T. Behavior of arterial wall cells cultured on periodically stretched substrates. *Cell Transplantation* 1993; 2: No. 6: 475–484.

Mooney DJ, et al. Design and fabrication of biodegradable polymer devices to engineer tubular tissues. *Cell Transplantation* 1994; 3: No. 2: 203–210.

Mooney DJ, et al. Stabilized polyglycolic acid fibre-based tubes for tissue engineering. *Biomaterials* 1996; 17: No. 2: 115–214.

Niklason L and Langer RS. Advances in tissue engineering of blood vessels and other tissues. *Transplant Immunology* 1997; 5: 303–306.

TISSUE-ENGINEERED TUBULAR CONSTRUCT HAVING CIRCUMFERENTIALLY ORIENTED SMOOTH MUSCLE CELLS

This application claims benefit of Provisional applications Ser. No. 60/052,553 filed Jul. 15, 1997, and Ser. No. 60/051,634 filed Jul. 3, 1997.

GOVERNMENT SUPPORT

This invention was made with government support under Grant Number BES-9525913 awarded by the National Science Foundation and Grant Number HL03492-02 awarded by the National Institute of Health. The government has certain rights in the invention.

FIELD OF THE INVENTION

The present invention is directed generally to the art of tissue engineering, or the production of organized mammalian tissues in vitro.

BACKGROUND OF THE INVENTION

Tissue engineering is emerging as a new field in the biomedical sciences. Langer and others have demonstrated the feasibility of seeding and culturing various cell types on biocompatible, biodegradable polymer films and three-dimensional scaffolds or substrates (Takeda et al. (1995); Vacanti et al. (1994); Mooney et al. (1994); Cao et al. (1994); Bell (1994); Gilbert et al. (1993); Freed et al. (1994a); Mooney et al. (1994); Cima et al. (1991); Cima and Langer (1993); Wintermantel et al. (1991); Mooney et al. (1992); Freed et al. (1994b); Freed et al. (1993)). Cell attachment, spreading and replication have been demonstrated to occur on these polymers, and the formation of solid tissue masses of up to one millimeter in thickness has been demonstrated for tissues such as cartilage (Freed et al. (1994a); Freed et al. (1994b); Freed et al. (1993)). Many cell types have been implanted successfully in vivo, including hepatocytes, chondrocytes, fibroblasts, enterocytes, smooth muscle cells and endothelial cells (Takeda et al. (1995); Mooney et al. (1994); Gilbert et al. (1993); Mooney et al. (1994)).

Tissue-engineered constructs may be used for a variety of purposes both in vivo and in vitro. For example, such constructs may serve as prosthetic devices for the repair or replacement of damaged organs or tissues, such as in coronary bypasses or liver grafts. In addition, tissue-engineered constructs can serve as in vivo delivery systems for proteins or other molecules secreted by the cells of the construct. Alternatively, tissue-engineered constructs can serve as in vitro models of tissue function or as models for testing the effects of various treatments or pharmaceuticals.

Of particular interest are vascular tissue-engineered constructs. There are 1.4 million surgical procedures performed annually in this country that require arterial prostheses (Langer and Vacanti (1993)). Small arteries with diameters less than five to six mm cannot be replaced with artificial materials due to high rates of thrombosis (Connolly et al. (1988); Greisler et al. (1988)). Thus, autologous vein or artery grafts are generally used to replace small arteries in the coronary or peripheral circulations. Vein grafts have thin walls that are sometimes damaged when transplanted into the arterial system, and suitable veins are not available in all patients due to amputation or previous vein harvest. Internal mammary arteries, which comprise the majority of arterial grafts, are useful only in the coronary circulation. Thus, there remains a need for developing methods for culturing autologous arterial grafts from a small biopsy of the patient's own tissue, or heterologous arterial grafts from histocompatible cells derived from a donor or cell line.

SUMMARY OF THE INVENTION

The present invention is directed to improved methods for the production of tissue-engineered constructs, including muscular tissue constructs such as vascular constructs. The methods include the use of improved substrates for cell growth, improved cell culture media for cell growth, and the use of distensible bodies to impart pulsatile stretching force to the lumens of constructs during growth. Also provided are improved products, including substrates and cell culture media, for tissue engineering and tissue culture generally. Improved muscular tissue constructs, including vascular constructs, are also provided, which may be used in medicine for the repair or replacement of damaged natural structures.

Thus, in one aspect, the invention provides a method for producing a muscular tissue-engineered construct in which a porous substrate, comprising a biocompatible material, and having an inner surface and an outer surface, is first provided. The inner surface of the porous substrate defines a lumen. Within the lumen, a distensible body is provided which is capable of distending within the lumen so as to contact the inner surface of the substrate. The porous substrate, either before or after inserting the distensible body, is contacted with a suspension comprising muscle cells which adhere to and infiltrate the porous substrate, thereby forming a primary cell-seeded construct. The primary cell-seeded construct is then maintained for a first growth period in an environment suitable for growth of the muscle cells to form a primary tissue-engineered construct. During the first growth period, cyclical increases in pressure within the distensible body are provided, thereby causing the distensible body to distend within the lumen of the construct and to apply pulsatile stretch to the construct. This pulsatile stretch mimics natural pulsatile stretching forces encountered in the body, and aids the growing construct in developing strength and/or an appropriate phenotype.

In another aspect, the invention provides a method for producing a muscular tissue-engineered construct in which a porous substrate comprising a biocompatible material, and having an inner surface and an outer surface, is first provided. The inner surface of the porous substrate defines a lumen. The porous substrate is contacted with a suspension comprising muscle cells which adhere to and infiltrate the porous substrate, thereby forming a primary cell-seeded construct. Rather than a distensible body within the lumen of the construct, a sleeve is provided, either before or after cell-seeding, around a portion of the exterior of the porous substrate. The sleeve is capable of resisting distension of the substrate in response to pressure within the lumen. The primary cell-seeded construct is then maintained for a first growth period in an environment suitable for growth of the smooth muscle cells to form a primary tissue-engineered construct. During the first growth period, intralumenal flow is provided within the lumen, thereby causing the substrate to distend within the sleeve, and to contact the sleeve. The sleeve, by resisting the distension, provides mechanical support to the growing construct. Optionally, during the first growth period, cyclical increases in pressure are also provided within the lumen, thereby causing the substrate to cyclically distend within the sleeve, and thereby applying pulsatile stretch to the construct. This intralumenal flow, and optional pulsatile stretch, mimic natural flow and pulsatile stretching forces encountered in the body, and aids the growing construct in developing strength and/or an appropriate phenotype.

In another aspect, the invention provides a method for producing a muscular tissue-engineered construct in which a porous substrate comprising a biocompatible material, and having an inner surface and an outer surface, is first provided. The inner surface of the porous substrate defines a lumen. Rather than a distensible body or sleeve, an inner surface of the lumen (or a medial layer of the substrate) is provided which is substantially less porous than the outer surface, and this inner surface (or medial layer) is also capable of resisting distension of the substrate in response to pressure within the lumen. The porous substrate is contacted with a suspension comprising smooth muscle cells which adhere to and infiltrate the porous substrate, thereby forming a primary cell-seeded construct. The primary cell-seeded construct is then maintained for a first growth period in an environment suitable for growth of the smooth muscle cells to form a primary tissue-engineered construct. During the first growth period, intralumenal flow within the lumen is provided, thereby causing the substrate to distend. The inner surface (or medial layer), by resisting the distension, provides mechanical support to the growing construct. Optionally, during the first growth period, cyclical increases in pressure are also provided within the lumen, thereby causing the substrate to cyclically distend, and thereby applying pulsatile stretch to the construct. This intralumenal flow, and optional pulsatile stretch, mimic natural flow and pulsatile stretching forces encountered in the body, and aids the growing construct in developing strength and/or an appropriate phenotype.

Preferably, in each of the above described embodiments, the porous substrate comprises a synthetic polymeric material having a hydrophilic surface, as described below.

In addition, optionally in each of the above-described embodiments, the methods include the additional steps of contacting the resulting primary cell-seeded construct or primary tissue-engineered construct with a suspension comprising a second type of mammalian cells capable of adhering to and/or infiltrating the substrate, thereby forming a secondary cell-seeded construct, and maintaining the secondary cell-seeded construct for a second growth period in an environment suitable for growth of the second type of cells to form a secondary tissue-engineered construct.

In preferred embodiments, the above-described muscular tissue-engineered constructs are vascular tissue constructs. Therefore, in these preferred embodiments, the porous substrate is a substantially tubular substrate, the first type of mammalian cells are smooth muscle cells, and the second type of mammalian cells are endothelial cells which are contacted with the inner surface of the lumen.

In each of the embodiments applying pulsatile stretch to the growing tissue construct, it is preferred that the pulsatile stretch causes an increase in an inner diameter of the construct of between approximately 1–10%, more preferably between approximately 2–6%.

The present invention also provides improved methods for producing a tissue-engineered construct, whether muscular or non-muscular, employing substrates which comprise biocompatible synthetic polymers having hydrophilic surfaces. Thus, in another aspect, the invention provides a method for producing a tissue-engineered construct in which a substrate, porous or non-porous, is provided which comprises a biocompatible synthetic polymer having a hydrophilic surface. The substrate is contacted with a suspension comprising a first type of mammalian cells which are capable of adhering to and/or infiltrating the substrate to form a primary cell-seeded construct. The primary cell-seeded construct is maintained for a first growth period in an environment suitable for growth of the mammalian cells to form a primary tissue-engineered construct. In these methods, it is found that the biocompatible synthetic polymers with hydrophilic surfaces result in much improved cell seeding densities and/or much improved cell density in the final tissue-engineered construct. Optionally, the resulting primary cell-seeded construct or said primary tissue-engineered construct is contacted with a suspension comprising a second type of mammalian cells which are capable of adhering to or infiltrating the construct to form a secondary cell-seeded construct, and this secondary cell-seeded construct is maintained for a second growth period in an environment suitable for growth of the second type of cells to form a secondary tissue-engineered construct.

In each of the foregoing embodiments, a variety of cells may be seeded onto the substrates. These include smooth muscle cells, epithelial cells, endothelial cells, fibroblasts, myoblasts, hepatocytes, bile duct cells, pancreatic islet cells, thyroid, parathyroid, adrenal, hypothalamic, pituitary, ovarian, testicular, or salivary cells, cardiac muscle cells, renal cells, chondrocytes, nerve cells, and progenitor cells.

In each embodiment described above, it is preferred that the polymeric substrate material comprises a polymer selected from polyesters of hydroxy carboxylic acids, polyanhydrides of dicarboxylic acids, or copolymers of hydroxy carboxylic acids and dicarboxylic acids. In particularly preferred embodiments, the polymeric material is selected from the polymers or copolymers of glycolic acid, lactic acid, and sebacic acid.

In those embodiments employing a porous substrate, it is preferred that the substrate comprises a porous mesh of fibers having diameters of between approximately 5–20 $\mu$m, preferably between approximately 10–15 $\mu$m, and most preferably about 13 $\mu$m. It is also preferred that the substrate comprises a porous mesh of fibers in which substantially parallel fibers in the mesh are separated by approximately 20–200 $\mu$m, preferably approximately 50–100 $\mu$m. It is also preferred that the porous substrate is characterized by a void volume of greater than 90%, preferably greater than 95%. It is also preferred that the substrate has an average pore size of less than 200 $\mu$m, preferably less than 175 $\mu$m, and more preferably less than 150 $\mu$m.

In those embodiments employing a substrate of polymeric material having a hydrophilic surface, it is preferred that the surface comprises a multiplicity of hydrophilic chemical groups selected from carboxyl, hydroxyl, thiol, amine, sulfonyl, guanidine, and amide groups. In preferred embodiments, these hydrophilic groups have a density of at least 5 pmol/cm$^2$, preferably at least 10 pmol/cm$^2$, and generally between 5 and 20 pmol/cm$^2$. It is also preferred that the hydrophilic surface has a contact angle of less than 20°, preferably less than 15°, more preferably less than 10°, and most preferably less than 5°.

In another aspect, the present invention provides for improved growth media for producing muscular tissue-engineered constructs. Therefore, in those embodiments described above in which smooth muscle cells are cultured, a standard cell culture medium is employed which is supplemented with about 0.01–0.1 g/L, preferably about 0.02–0.06 g/L, of at least one amino acid selected from proline, glycine, and alanine. In addition, a standard cell culture medium is employed which is supplemented with about 0.01–0.1 g/L, preferably about 0.02–0.06 g/L, of vitamin C. Further, a standard cell culture medium is employed which is supplemented with about 0.5–5.0 µg/L, preferably about 1.0–3.0 µg/L, of a copper salt.

In another aspect, the present invention provides substrates for use in tissue culture, which comprise three-dimensional scaffolds of a biocompatible synthetic polymer having a hydrophilic surface. As described above, these substrates preferably comprise a polymer selected from the polyesters of hydroxy carboxylic acids, polyanhydrides of dicarboxylic acids, and copolymers of hydroxy carboxylic acids and dicarboxylic acids. Most preferably, the polymeric material is selected from the polymers or copolymers of glycolic acid, lactic acid, and sebacic acid. In those embodiments in which the substrate is a porous substrate, it is preferred that the substrate comprises a porous mesh of fibers having diameters of between approximately 5–20 µm, preferably between approximately 10–15 µm, and most preferably about 13 µm. It also preferred that the substrate comprises a porous mesh of fibers in which substantially parallel fibers in the mesh are separated by approximately 20–200 µm, preferably approximately 50–100 µm. It is also preferred that the porous substrate is characterized by a void volume of greater than 90%, preferably greater than 95%. It is also preferred that the substrate has an average pore size of less than 200 µm, preferably less than 175 µm, and more preferably less than 150 µm.

In particularly preferred embodiments, a substrate is provided comprising a biocompatible polymeric material with a hydrophilic surface hydrophilic, in which the surface comprises a multiplicity of hydrophilic chemical groups selected from the carboxyl, hydroxyl, thiol, amine, sulfonyl, guanidine, and amide groups. It preferred that these hydrophilic groups have a density of at least 5 pmol/cm$^2$, preferably at least 10 pmol/cm$^2$, and generally between 5 and 20 pmol/cm$^2$. It is also preferred that the hydrophilic surface has a contact angle of less than 20°, preferably less than 15°, more preferably less than 10°, and most preferably less than 5°.

In another aspect, the present invention provides substrates for cell culture and tissue-engineering, and methods for making such substrates, in which the substrate comprises a multiplicity of polyester or polyanhydride bonds, and the hydrophilic surface is formed by at least partial hydrolysis of the bonds at the surface.

In another aspect, the present invention provides a muscular, tubular tissue-engineered construct comprising a substantially tubular construct of living mammalian tissue having a first end and a second end, an inner surface and an outer surface. In these constructs, the first end, the second end, and the inner surface of the construct define a lumen passing through the construct, and the tissue between the inner surface and outer surface defines a wall of the construct. The wall comprises mammalian smooth muscle cells oriented circumferentially about the lumen.

In preferred embodiments, a muscular tissue-engineered construct is provided in which the smooth muscle cells in the wall have a cell density of at least 10$^7$ cells/cc, preferably at least 10$^8$ cells/cc. It is also preferred that the tubular construct is capable of withstanding, for a sustained period without rupturing (e.g., at least one hour), an internal pressure of at least 100 mm Hg, preferably at least 110 mm Hg, more preferably at least 120 mm Hg, and most preferably at least 130 mm Hg. It is also preferred that the tubular construct is capable of withstanding, for a sustained period without rupturing, an internal shear force of at least 5 dynes/cm$^2$, preferably at least 10 dynes/cm$^2$, more preferably at least 20 dynes/cm$^2$, and most preferably at least 30 dynes/cm$^2$. In other aspects, the present invention provides such constructs in which the wall further comprises a synthetic polymeric material, in which the outer surface is substantially free of an adventitia, in which the wall is substantially free of an intermediate layer of an intima, in which the wall is substantially free of an internal elastic lamina of an intima, in which the wall is substantially free of fibroblasts in an intimal layer, and/or in which the wall is substantially free of fibroblasts in a medial layer.

These and other aspects of the present invention will be apparent to one of ordinary skill in the art from the following detailed description of the invention and certain preferred embodiments.

DETAILED DESCRIPTION OF THE INVENTION

I. DEFINITIONS

Figure 1:
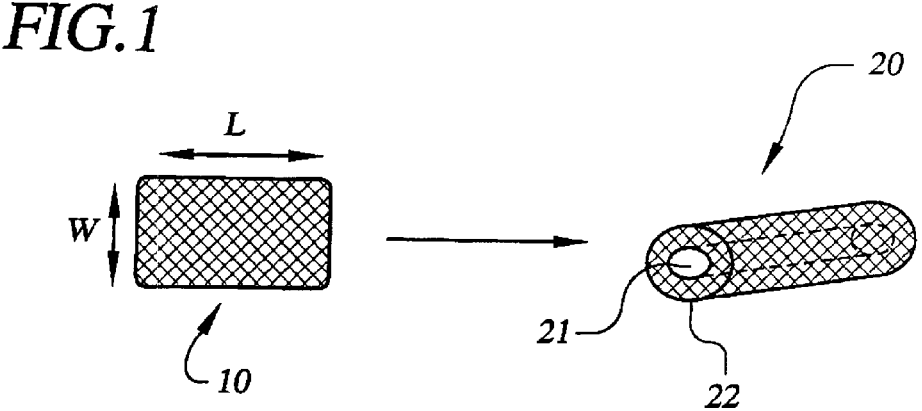
FIG. 1 shows a porous substrate (10) which is rolled and sealed along its length (1) to form a substantially tubular construct (20) having an outer surface (22) and an inner surface (21) defining a lumen.

In order to more clearly and concisely point out the subject matter of the claimed invention, the following definitions are provided for specific terms used in the following written description and appended claims.

Tissue-engineered construct. As used herein, a "tissue-engineered construct" means a three-dimensional mass of living mammalian tissue produced primarily by growth in vitro. The construct may include one or more types of tissue, and each tissue may include one or more types of cells. A tissue-engineered construct is distinguished from an explant of a corresponding natural tissue in that the primary the growth of the construct occurs in vitro.

Porous substrate. As used herein, a "porous substrate" means a three-dimensional substrate of a biocompatible material which is suitable for attachment or adherence of mammalian cells, and which is sufficiently porous to allow for the infiltration of seeded cells, and the diffusion of nutrients and waste products to and from cells adhered to the substrate, including cells adhered within the interior pores or interstitial spaces of the substrate. Thus, a porous substrate has pores or interstitial spaces interspersed through its structure, and in fluid communication with the exterior, such that cells may infiltrate into the interior of the substrate. The pores or interstitial spaces may be roughly spheroidal spaces, such as the pores in a sponge-like material, or may be longitudinally extended and intersecting spaces, such as the inter-fiber spaces in a fibrous mesh material, or may be of any other arbitrary shape. As used herein, no distinction is made between the "pores" of sponge-like materials, the "interstitial spaces" of fibrous mesh materials, or the arbitrarily shaped "spaces" of any other materials, and the term "porous" embraces materials characterized by any of these.

Synthetic polymer. As used herein, the term "synthetic polymer" means a non-naturally occurring polymer made by, for example, ex vivo synthesis, and physically distinguishable from naturally occurring polymers. Thus, the term is used herein merely to distinguish synthetic polymers, such as those described and enabled herein, from such naturally-occurring polymers as collagen, elastin, polysaccharides, cellulose, chitosan, and the like. A synthetic polymer may include one or more naturally-occurring subunits, such as naturally occurring amino acids or saccharide units, in an otherwise non-natural polymer (e.g., copolymers of lysine or arginine with lactic acid or glycolic acid).

Proteinaceous polymer. As used herein, the term "proteinaceous polymer" means a polymer consisting essentially of naturally-occurring or chemically modified amino acids residues joined by peptide linkages. Proteinaceous polymers of the invention may be naturally-occurring polymers which are extracted from animal tissues (e.g., collagen obtained from connective tissues), may be recombinantly produced polymers obtained from genetically engineered organisms (e.g., bacteria engineered to produce elastin), or may be produced in vitro by chemical synthesis. Thus, for example, as used herein, the term embraces such naturally-occurring proteinaceous polymers as collagen, elastin, fibronectin, laminin and the like. A proteinaceous polymer may also include one or more non-naturally-occurring subunits, such as modified amino acids (e.g., acylated, sulfonated, glycosylated, or otherwise conjugated through reactive amino acid side chain groups to moieties which increase hydrophilicity or provide better cell-adhesion characteristics), or may include non-peptide linkages joining two or more proteinaceous fragments (e.g., polypeptides or modified polypeptides copolymerized with polyesters, polyanhydrides).

Hydrophilic surface. As used herein, a "hydrophilic surface" means a surface which is "wettable" as that term is used in the art, or which, when subjected to a sessile drop wettability test, displays a contact angle with water of less than 90°. More preferably, a hydrophilic surface is one which displays a contact angle of less than 45°, 20°, 10°, or 5°. As used herein, a "contact angle" means the solid-liquid-gas contact angle where the solid is the relevant polymer, the liquid is water, and the gas is air. The value of the contact angle directly reflects the surface and interfacial energies based on Young's equation (see, e.g., Adamson, ed. (1990) *Physical Chemistry of Surfaces*, 5th Edition, John Wiley & Sons, Inc., New York, pp. 379–420).

Distensible body. As used herein, a "distensible body" means a hollow body comprising a resilient material which, when subjected to repeated and sufficient increases/decreases in pressure within the interior of the body, can expand/contract so as to increase/decrease in an exterior dimension by at least 4–6%, preferably 4–10%, and more preferably 4–20%, without rupturing. A distensible body will have one or more openings by which it is attached to means for increasing the internal pressure, such as a tubing connected to a fluid pump. Examples of distensible bodies include distensible tubes which are substantially cylindrical in shape, and distensible bladders which may be substantially spheroidal or ellipsoidal in shape. Thus, for example, the term "distensible tube" includes substantially cylindrical devices made of a resilient material which, when subjected to repeated and sufficient increases in pressure within the interior of the tube, can distend or expand so as to increase circumferentially in diameter by at least 4–6%, preferably 4–10%, and more preferably 4–20%, without rupturing.

Muscular. As used herein with reference to tissue engineered-constructs, the term "muscular" describes a tissue comprising or consisting of mammalian muscle cells which have grown substantially to confluence, and which can exert contractile force. In certain preferred embodiments, the muscle cells are smooth muscle cells. Skeletal muscle or cardiac muscle cells, however, may also be employed in the present invention.

Pulsatile stretch. As used herein, "pulsatile stretch" means a circumferential stretching or expansion of a substantially tubular object or construct, similar to the circumferential stretching or expansion of an artery in response to the cyclical increases and decreases in blood pressure caused by the beating of a heart.

Environment suitable for growth. As used herein, an "environment suitable for growth" of a particular cell type means an environment with conditions of temperature, pressure, nutrient and waste exchange, and gas exchange, which are permissive for the survival and reproduction of the cells. With respect to any particular type of cells, an environment suitable for growth may require the presence of particular nutrients required by that cell type, or the presence of particular growth factors necessary for the survival and reproduction of those cells.

II. GENERAL CONSIDERATIONS

The present invention provides several novel advances in methods and products for use in the field of tissue engineering. In particular, the present invention provides new porous substrates for the growth of mammalian cells which may be seeded onto and into these substrates. In addition, the present invention provides for new methods of producing muscular tissue-engineered constructs with lumens, in which a distensible body contained within the lumen of the growing construct applies a pulsatile force to growing tissue. This pulsatile force mimics, in part, the forces encountered by the cells in natural arterial and venous walls, the alimentary canal, ureters, the bladder, and other biological structures which include circumferentially or peripherally oriented rings of muscle. The use of a pulsatile force in the present invention aids in the organization of muscle cells into circumferential rings in the wall of the construct, as well as the development or maintenance of a contractile phenotype by these cells. In addition, the present invention provides for new growth media and methods for their use in the production of tissue-engineered constructs. These new growth media are believed to enhance the production of an appropriate extracellular matrix in the tissue-engineered construct, thus increasing its strength.

Thus, according to one aspect of the present invention, a method for producing a tissue-engineered construct is provided in which a porous substrate comprising a synthetic, polymeric, biocompatible material is contacted or "seeded"

with a suspension of a first type of mammalian cells to form a primary cell-seeded construct, and this cell-seeded construct is maintained for a first growth period in an environment suitable for growth of the cells to form a primary tissue-engineered construct. The porous substrate may be of essentially any size or shape, may be a sponge-like porous material or may be a fibrous mesh. Importantly, in this aspect of the invention, the substrates have hydrophilic surfaces, as described in more detail below, which permit cells to be seeded at a higher density, resulting in a higher final density of cells in the final tissue-engineered construct. The porous substrates of the invention are seeded with cell suspensions including at least one type of cell, but may be seeded with suspensions comprising a mixture of cells (e.g., hepatocytes and fibroblasts) to create a more complex primary tissue construct. After a first period of growth, the resulting primary tissue construct may optionally be seeded with a second suspension of cells including at least one cell type, and this secondary cell-seeded construct may be maintained for a second growth period to produce a secondary tissue-engineered construct. Further rounds of cell-seeding and growth may, of course, be employed. In addition, between any growth period and the next step of cell-seeding (e.g., after production of the primary tissue-engineered construct, but before production of a secondary cell-seeded construct), additional substrate material may be added, or the tissue-engineered construct may be inserted within a larger substrate. In this way, a complex organ-like structure may be produced by, for example, first producing a vascular tissue-engineered construct (by one or more rounds of cell-seeding and growth) and then embedding this in a larger substrate to produce, for example, a liver or other glandular tissue-engineered construct which will include an internal, tissue-engineered vascular system.

The present invention also provides novel methods particularly directed to the production of a muscular tissue-engineered construct. In these methods, a porous substrate, comprising a biocompatible material and defining a lumen, is contacted or "seeded" with a suspension including muscle cells (preferably, but not necessarily, smooth muscle cells) to form a primary cell-seeded construct, and this cell-seeded construct is maintained for a first growth period in an environment suitable for growth of the cells to form a primary tissue-engineered construct. In addition, however, a distensible body is provided, before or after seeding the muscle cells, within the lumen of the porous substrate. The distensible body is chosen to have a shape substantially similar to the shape of the lumen, and is capable, upon distension, of contacting the inner surface of the substrate (i.e., the walls of the lumen) so as to apply pulsatile stretching forces to, and cause distension of, the substrate. Preferably, the distensible body has outer dimensions approximately equal to the inner dimensions of the lumen. During the first growth period, cyclical increases in pressure within the distensible body are provided, thereby causing the body to distend within the lumen of the construct and to apply pulsatile stretch to the construct. In addition, the primary cell-seeded construct is preferably maintained in a growth medium which includes certain factors, described in more detail below, which enhance the development of the muscle cell layer. Optionally, after the first growth period, the resulting primary tissue-engineered construct may be seeded with a second suspension of cells including at least one cell type (e.g., endothelial cells applied to the outer and inner surfaces of the primary tissue-engineered construct), and this secondary cell-seeded construct may be maintained for a second growth period to produce a secondary tissue-engineered construct. During this second growth period, the distensible body may continue to be used to apply a pulsatile stretch or, if the primary tissue-engineered construct has sufficient strength, the distensible body may be removed and fluid flow may be maintained directly through the lumen, with or without additional pulsatile stretching. As above, further rounds of cell-seeding and growth may be employed, and the tissue-engineered construct resulting from any growth period may be incorporated into a larger porous substrate and seeded to produce a more complex organ-like construct.

In most preferred embodiments, the porous substrate is substantially tubular or cylindrical in shape, and the distensible body is a distensible tube. The resulting muscular tissue-engineered construct is characterized by circumferentially oriented rings of muscle, and the construct can form the basis of a vascular tissue-engineered construct or prosthesis, preferably with an inner lining of endothelial cells. Muscular, tubular constructs may also be produced for esophageal, intestinal, rectal, and ureteral prostheses.

These and other objects and advantages of the present invention are described in more detail in the preferred embodiments and examples below.

III. PREFERRED EMBODIMENTS

A. Porous Substrates for Tissue-Engineered Constructs

The porous substrates of the present invention may be any three dimensional structure comprising a biocompatible material which is sufficiently porous to allow for infiltration of seeded cells and diffusion of nutrients and waste products to and from cells adhered to the surface, including the inner surfaces, of the substrate. The feasibility of seeding and culturing various cell types on biocompatible, biodegradable substrates, including polymer films and three-dimensional scaffolds, has been demonstrated in the art (Takeda et al. (1995); Vacanti et al. (1994); Mooney et al. (1994); Cao et al. (1994); Bell (1994); Gilbert et al. (1993); Freed et al. (1994a); Mooney et al. (1994); Cima et al. (1991); Cima and Langer (1993); Wintermantel et al. (1991); Mooney et al. (1992); Freed et al. (1994b); Freed et al. (1993)). In accordance with the present invention, the substrate may be formed in essentially any shape including, but not limited to, solid porous substrates such as spheres, ellipsoids, disks, sheets or films, as well as hollow porous substrates such as hollow spheres or ellipsoids, and open-ended tubes. In preferred embodiments for muscular, tubular tissue-engineered constructs, the substrates comprise substantially tubular or cylindrical shapes, including tubular shapes with diameters which vary along the length of the substrate.

Preferably, the substrate material comprises a biodegradable or bioerodable material, such as one which is slowly hydrolyzed under physiological conditions. Thus, generally, any biocompatible, slowly hydrolyzable polymers may be employed. Preferred substrate materials include polymeric materials such as polyesters, polyorthoesters, or polyanhydrides, including polymers or copolymers of glycolic acid, lactic acid, or sebacic acid. More generally, preferred substrate materials include polyesters of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy hydroxy acids (e.g., $(COOH)(CH_2)_n(OH)$ or $(COOH)(CR_iR_j)_n(OH)$, where n is an integer between about 1 and 20, and each $R_i$ and $R_j$ is independently selected from the group consisting of —H, —OH, —SH, —NH$_2$, the halogens, the side chains of the naturally occurring amino acids, and any straight chain or branched, substituted or unsubstituted, saturated or unsaturated, low molecular weight (e.g., $C_1$–$C_{14}$) alkanyl, haloalkyl, thioalkyl, aminoalkyl, aryl, aralkyl, alkenyl, aralkenyl, heteroaryl, or alkoxy group, or a secondary or tertiary amine substituted with such groups) or polyanhydrides of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy dicarboxylic acids (e.g., (COOH)(CH$_2$)$_n$(COOH) or (COOH)(CR$_i$R$_j$)$_n$(COOH), where n is an integer between about 1 and 20, and each R$_i$ and R$_j$ is independently selected from the group consisting of —H, —OH, —SH, —NH$_2$, the halogens, the side chains of the naturally occurring amino acids, and any straight chain or branched, substituted or unsubstituted, saturated or unsaturated, low molecular weight (e.g., $C_1$–$C_{14}$) alkanyl, haloalkyl, thioalkyl, aminoalkyl, aryl, aralkyl, alkenyl, aralkenyl, heteroaryl, or alkoxy group, or a secondary or tertiary amine substituted with such groups). Polymers including mixtures of ester and anhydride bonds (e.g., copolymers of glycolic and sebacic acid) may also be employed. Thus, for example, preferred substrate materials include polyglycolic acid polymers (PGA), polylactic acid polymers (PLA), polysebacic acid polymers (PSA), poly (lactic-co-glycolic) acid copolymers (PLGA), poly(lactic-co-sebacic) acid copolymers (PLSA), poly(glycolic-co-sebacic) acid copolymers (PGSA), etc.

Other biocompatible biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials. The currently preferred biodegradable materials are PLA, PGA, and PLGA polymers. See, generally, U.S. Pat. Nos. 1,995,970; 2,703,316; 2,758,987; 2,951,828; 2,676,945; 2,683,136 and 3,531,561.

Biocompatible but non-biodegradable materials may also be used in the porous substrates of the present invention. For example, non-biodegradable polymers of acrylates, ethylene-vinyl acetates, acyl substituted cellulose acetates, non-degradable urethanes, styrenes, vinyl chlorides, vinyl fluorides, vinyl imidazoles, chlorosulphonated olefins, ethylene oxide, vinyl alcohols, TEFLON® (DuPont, Wilmington, Del.), and nylons. See, generally, U.S. Pat. Nos. 2,609,347; 2,653,917; 2,659,935; 2,664,366; 2,664,367; and 2,846,407.

As an alternative to synthetic polymer substrates, porous substrates may be employed which comprise proteinaceous polymers. Such substrates are known in the art and have been used in the production of tissue-engineered constructs. For example, collagen gels have been used to produce vascular tissue constructs (Weinberg and Bell, (1986)), and collagen sponges and meshes are now commercially available (e.g., from Ortec International, Inc., New York, N.Y.). Such collagenous substrates, as well as similarly constructed substrates based on elastin, fibronectin, laminin, or other extracellular matrix or fibrillar proteins, may be employed in the methods and constructs of the present invention. Such proteinaceous polymer substrates may be in the form of fibrous meshes, as described above, or may be in the form of non-fibrous substrates such as sheets, films, or sponges. In addition, these substrates may include proteinaceous polymers which have been modified by, for example, acylating, sulfonating, glycosylating, or otherwise conjugating reactive groups of the amino acid side chains with other moieties to increase hydrophilicity and/or provide better cell-adhesion characteristics. For example, the proteins may be acylated with dicarboxylic acid anhydrides to increase hydrophilicity, or may be conjugated to cell-adhesion peptides to increase the density or avidity of cell-seeding. Such proteinaceous polymers have the advantage that they are completely biological in nature and, therefore, will have reduced immunogenicity if syngeneic to the host.

The porous substrate may comprise a randomly cross-linked material in the form of a sponge or, preferably, may comprise a porous mesh of fibers. For example, in preferred embodiments, the substrate comprises a porous mesh of fibers having a diameter of between approximately 5–20 $\mu$m, between approximately 10–15 $\mu$m, or approximately 13 $\mu$m. Such fibrous polymeric materials are known in the art and are commercially available (e.g., fibrous PGA polymers sold as DEXON® (Sherwood Davis & Geck, Hampshire, UK), and fibrous PLGA polymers sold as VICRYL® (Ethicon, Edinburgh, Scotland) which have been approved by the U.S. Food and Drug Administration for clinical use (Freed et al. (1994)). The physical characteristics and degradation rates of these polymers are known in the art (Gilding and Reed (1979)). The fibers may be solid or hollow, and may comprise a multiplicity of materials (e.g., a solid fiber of two materials, or a hollow fiber of one material and a core of another).

When a porous substrate is formed of a mesh of fibers, adjacent substantially parallel fibers, or adjacent substantially parallel portions of fibers, are preferably separated, on average, by approximately 20–200 $\mu$m or, more preferably, approximately 50–100 $\mu$m, to define pores or interstitial spaces which have similar dimensions. When a porous substrate is formed of a sponge-like material, the pores are preferably, on average, approximately 20–200 $\mu$m or, more preferably, approximately 50–100 $\mu$m, in each cross-sectional dimension. The pores of the porous substrate will define a void volume, as that term is known in the art. To allow for a high density of cell seeding within the pores or interstitial spaces of the substrate, the porous substrate of the present invention is characterized by a void volume of greater than at least 80%, preferably 90% or, more preferably, greater than 95%. Most preferably, the void volume is about 97%.

In one aspect of the present invention, improved tissue-engineered constructs are provided by employing a porous substrate with a hydrophilic surface. Without being bound to any particular theory of the invention, it is believed that the hydrophilic surface aids in the attachment or adherence of certain cell types, including smooth muscle cells, to the substrate. Such a hydrophilic surface preferably comprises a multiplicity of hydrophilic chemical groups such as carboxyl, hydroxyl, thiol, amine, sulfonyl, guanidine, and amide groups. When the porous substrate comprises a polyester, polyorthoester or polyanhydride material, a hydrophilic surface may conveniently be prepared by hydrolyzing the outer surface of the fibers (e.g., by treatment with a base) to cause ester or anhydride bonds accessible at the surface to be hydrolyzed to carboxyl and/or hydroxyl groups. These groups may be further derivatized, if desired, to thiol, sulfonyl, guanidine, amine or amide groups by standard organic chemical techniques, and cell adhesion peptides may also be bound to the surface. For example, Barrera and co-workers (Barrera et al. (1993)) have synthesized a copolymer of lactic acid and lysine that allows for the covalent attachment of cellular adhesion peptides to the polymer backbone. The peptide arginine-glycine-aspartic acid (RGD), which is a cell-binding domain of fibronectin, as well as several other cell adhesion molecules (Massia and Hubbell (1990)), have been covalently bound by their N-termini to the lysine moieties of this copolymer. Preferred cell-adhesion peptides for use in the present invention include the sequences RGD and REDV (which is preferred for binding endothelial cells).

The hydrophilicity of the surface of the substrate material may be conveniently analyzed by measuring the contact angle of water drops on the surface of a film of the material using the sessile drop method (e.g., employing a Video Contact Angle System, ASC, Inc.). A hydrophilic surface is one in which the contact angle is less than 90°. Preferably, however, the hydrophilic surface has a contact angle of less than 45°, 20° or 10°. In most preferred embodiments, the contact angle is less than 5°.

As noted above, in preferred embodiments the substrate comprises a biodegradable material such that, after a sufficient period of growth, the resulting tissue-engineered construct is substantially free of any remaining substrate material. For example, the degradation of a PGA substrate material having fiber diameters of approximately 13 $\mu$m was measured without cultured cells in phosphate buffered saline at 37° C. Under such conditions, PGA undergoes bulk-hydrolysis that appears to have first order kinetics in two stages. Approximately 50% of the mass degraded within 1–4 weeks. Even after many weeks (e.g., 3–8 weeks), however, traces of the matrix material may still be observed microscopically. By varying the thickness of the fibers, as well as their chemical composition, one of ordinary skill in the art can readily produce biodegradable polymeric fibers, as described above, having essentially any desired degradation characteristics. In addition, to reduce the mass of the substrate material, and therefore its degradation time, without reducing the surface area initially available for cell adherence, hollow fibers, fibers with a core of more readily degradable material, or fibers with a core filled with a biocompatible solution, may be employed. In general, it is preferred that a substrate of biodegradable material is employed such that, when the tissue growing on the construct has reached a density of approximately $1-3\times10^8$ cells/cc, approximately 70–100% of the substrate material is substantially degraded.

Finally, it should be noted that the degradation products of some substrate materials may have some adverse effects on cell growth even if the substrate material itself is biocompatible. Thus, for example, the hydrolytic degradation of polymers of organic acids (e.g., PGA, PGLA) releases free acids which, at the least, lower the pH in the local environment and may also have other physiological effects. Therefore, it may be desirable to include within a substrate material a neutralizing agent which will, at least partially, offset the effects of substrate degradation. For example, copolymers of organic acids and bases may be produced such that the degradation products tend to titrate or buffer each other. In the case of polymers of organic acids, a base such as lysine or arginine (or any other biocompatible base) may be included in a copolymer (e.g., a glycolic acid-lactic acid-lysine copolymer). Alternatively, if a hollow fiber is employed, the core may be filled with an alkaline solution or alkaline degradable material to offset the increase in acidity caused by fiber degradation.

B. Variations on Substrate Structures

As noted above, the porous substrates of the present invention may assume essentially any shape. In particularly preferred embodiments, however, tubular substrates are utilized. In addition, "compound" substrates comprising more than one substrate material are also useful in many embodiments. Thus, for example, a compound substrate may be produced which comprises a first porous substrate material joined to a second porous substrate material, in which the two materials differ in some characteristic such as biodegradability, pore size, void volume, or hydrophilicity. Alternatively, a porous substrate may be joined to a non-porous substrate, such as a film, to form a compound substrate in which the two materials may differ not only in their porosity, but also in other characteristics such as biodegradability or hydrophilicity. Such compound substrates may be seeded in one portion (e.g., a porous portion) with one type of cells, and in another portion (e.g., a non-porous portion) with a different type of cells. The different portions may be seeded with cells simultaneously, or at different times (e.g., after one or more growth periods). In addition, the compound substrate can be formed after one or more rounds of cell seeding and growth, by adding a new substrate portion to a primary (or later) tissue-engineered construct.

In a preferred embodiment for producing muscular, tubular tissue-engineered constructs, a compound substrate is employed. Thus, referring to FIG. 1, a rectangular piece of porous mesh material (10) having a length (l) and width (w) is rolled along its length to form a substantially tubular porous substrate (20), with an outer surface (22), and an inner surface (21) defining a lumen. The edges along the length (l) of the mesh (10) are joined in any appropriate manner (e.g., by sewing with uncoated PGA suture (Davis & Geck, Inc., Manati, P. R.), or by chemical bonding) to form the tubular construct (20). The construct may be of arbitrary length, but porous substrates of 1–20 cm are currently contemplated as being most useful. The width of the substrate material is also arbitrary, but is chosen to produce a tubular substrate with an inner lumen having a diameter useful for the intended purpose. For vascular tissue constructs, it is currently contemplated that inner lumens of 2–10 mm or, preferably, 3–6 mm will be most useful. For esophageal, intestinal, or rectal constructs, correspondingly larger lumens would be employed. The thickness of the substrate (i.e., the distance between the inner (21) and outer (22) surfaces) is chosen depending upon the desired thickness of the resulting tissue engineered construct. For vascular tissue constructs, a thickness of between 0.25–2.5 mm or, preferably, about 0.5–2.0 mm is currently contemplated as being most useful. As will be obvious to one of skill in the art, the tubular substrate (20) need not be formed by rolling a flat mesh to form a tube but, rather, can be produced as a single piece by, for example, weaving or extrusion.

Figure 2:
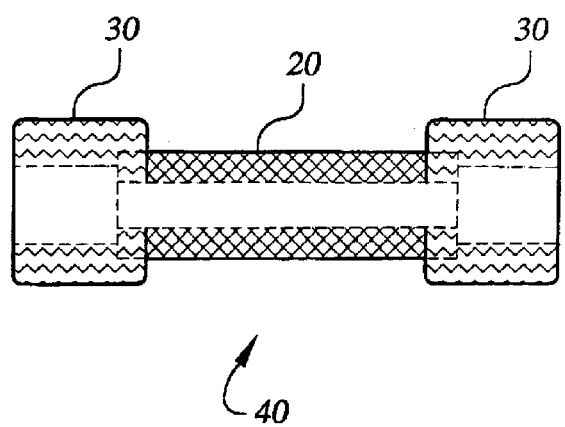
FIG. 2 shows a tubular construct (20) and cuffs (30) in which the diameter of the inner surface (31) of each cuff (30) is approximately equal to the outer diameter of the tubular construct (20). A cuff (30) may be attached to each end of the tubular construct (20) to form the compound construct (40).

Next, as the tubular porous construct (20) is preferably made of a biodegradable material, additional porous tubular portions or "cuffs" (30) made of a non-biodegradable material are optionally but preferably added to each end of the first construct to facilitate attachment of the construct to the bioreactor system. Thus, referring to FIG. 2, two substantially tubular cuffs (30) made of a non-biodegradable material, such as a porous Dacron vascular graft material (Bard Vascular Systems Division, Haverhill, Mass.), are attached to the ends of the first tubular construct (20) by any appropriate means (e.g., suture or chemical bonding) to form a compound construct (40). Note that the inner surface (31) of the cuffs (30) defines a diameter which is preferably chosen to be approximately equal to the diameter of the outer surface (22) of the porous substrate tube (20). The cuffs (30) are preferably chosen to be porous so that they may also be cell-seeded and form a substantially continuous layer of cells with those seeded onto the central portion (20) of the construct (40). Importantly, however, as the biodegradable substrate of the central portion (20) dissolves during cell culture and growth, the non-degradable substrate material of the cuffs (30) remains to add strength to the ends of the tissue construct. This strength is helpful in attaching the construct to the flow apparatus described below, but the cuff portion may be removed at a later time (e.g., for implantation in vivo) if desired.

Figure 3:
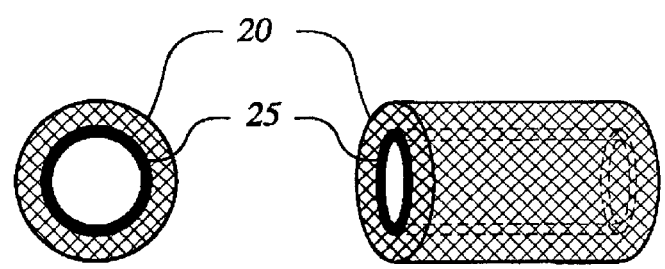
FIG. 3 shows a tubular construct (20) made of one substrate material, and a layer or film (25) of a second substrate material within the lumen of the tubular construct (20). This compound substrate construct is shown in cross-sectional (left) and side (right) views.

More complex substrate structures are also contemplated. For example, the porous mesh material (10) need not be uniform in composition, such that the inner surface (21), the outer surface (22), and/or the substrate material between these surfaces, differ in some characteristic such as biodegradability, pore size, void volume, or hydrophilicity. Thus, when used for the production of muscular, tubular tissue-engineered constructs, it is contemplated that a substrate material which degrades more slowly, has smaller pores, and/or has lower void volume may be preferred for one or more surfaces. In particular, if intralumenal flow is desired (with or without the presence of a distensible tube or sheath and pulsatile stretching force), it may be desirable to have the inner surface (21) of the tubular construct degrade more slowly, have smaller pores, and/or have a lower void volume. Alternatively, a substrate film (25) which is non-porous or slightly porous may be inserted within the lumen of a tubular construct (20) and contacted with or affixed to the inner surface (21) to form a compound substrate with an inner film and outer porous portion, as shown in FIG. 3. For example, a tubular porous mesh of PGA or PGLA fibers having diameters of 5–20 $\mu$m, as described above, may be provided with an inner film of PGA, PGLA, or a protein (e.g., collagen, elastin, fibronectin, laminin,) having a thickness of 5–50 or, preferably 10–30 $\mu$m. The desired thickness of the inner film depends, at the least, upon the material from which it is made, the culture conditions, and the desired length of time before the film substantially degrades. Alternatively, or in addition, such films may be added to the outer surface (22) of the tubular construct (20).

C. Cell-Seeding and Growth in Tissue-Engineered Constructs

A number of different cell types or combinations thereof may be employed in the present invention, depending upon the intended function of the tissue-engineered construct being produced. Thus, for example, smooth muscle cells and endothelial cells may be employed for muscular, tubular tissue-engineered constructs (e.g., vascular, esophageal, intestinal, rectal, or ureteral constructs); hepatocytes and bile duct cells may be employed in liver tissue-engineered constructs; pancreatic islet cells may be employed in pancreatic tissue-engineered constructs; thyroid, parathyroid, adrenal, hypothalamic, pituitary, ovarian, testicular, or salivary secretory cells may be employed in corresponding glandular tissue-engineered constructs; cardiac muscle cells may be employed in heart tissue-engineered constructs; renal cells may be employed in kidney tissue-engineered constructs; chondrocytes may be employed in cartilaginous tissue-engineered tissue constructs; and epithelial, endothelial, fibroblast and nerve cells may be employed in tissue-engineered constructs for the great variety of tissues in which these cells are found. More generally, any cells may be employed which are found in the natural tissue to which the tissue-engineered construct is intended to correspond. In addition, progenitor cells, such as myoblasts or stem cells, may be advantageously employed to produce their corresponding differentiated cell types in a tissue-engineered construct.

Thus, for example, natural arteries are comprised of endothelial, smooth muscle, and fibroblast cells organized into three layers: the intima, the media and the adventitia. The intima is composed primarily of endothelial cells and has three parts: the endothelium, an intermediate layer, and the internal elastic lamina. The media of small arteries consists of 25 to 40 layers of circumferentially disposed smooth muscle fibers between layers of connective tissue, while the media of veins contain relatively fewer (e.g., 5–20) layers of smooth muscle. Fibroblasts appear primarily in the adventitia in vivo and are not major components of the normal intimal or medial layers. Therefore, a vascular tissue-engineered construct will preferably include each of these cell types. Smooth muscle cells, for example, may be seeded onto a porous substrate to form a primary cell-seeded tissue construct which is allowed to grow for a first period to form a primary tissue-engineered construct. A low percentage of fibroblasts may also be included in this initial construct to increase the strength of the resulting construct. Endothelial cells may then be seeded onto the inner surface or lumen and, optionally, onto the outer surface of the construct to form a secondary cell-seeded construct. After a second growth period, this will produce a secondary tissue-engineered construct having a layer of smooth muscle cells (and, optionally, fibroblasts) between layers of endothelial cells.

Preferably, the cells are obtained from a live donor and cultured as a primary cell line. In particular, if the tissue-engineered construct is intended to be implanted into a living host, the cells are preferably harvested from the intended host or a histocompatible donor, thereby minimizing or eliminating the possibility of tissue rejection. For example, the required cells may be obtained from a biopsy of the patient. Thus, in the case of a patient requiring a coronary by-pass procedure, a biopsy of an artery (e.g. subclavian, axillary, brachial, radial, iliac, ulnar, femoral, anterior or posterior tibial) or peripheral vein (e.g., cephalic, basilic, saphenous, femoral) may be used to obtain arterial smooth muscle, endothelial and fibroblast cells. Alternatively, in the case of a patient requiring, for example, a liver, pancreatic, ureteral, esophageal, intestinal, rectal or other tissue-engineered implant, appropriate cells may be obtained by biopsies of these tissues. It should also be noted that, although not necessarily preferred, biopsies from tissues or organs which do not correspond to the intended implant, but which are phenotypically similar, may be employed. For example, smooth muscle cells derived from an artery may be employed in producing the smooth muscle layers of a venous, esophageal, intestinal, rectal, cardiac or ureteral tissue-engineered construct.

To obtain cells from a donor, standard biopsy techniques known in the art may be employed. Briefly, a desired tissue is surgically removed and the tissue is minced or homogenized, optionally with protease (e.g., trypsin or collagenase) treatment, and a suspension of dissociated cells, or small aggregates of cells, is prepared. Optionally, the cells may then be cultured in vitro in a standard cell growth medium until a suitable number or density of cells are obtained. Although cells may be passaged many times in such cultures, such passaging often causes a loss of differentiated phenotype and, therefore, it is preferred that the number of passages be limited to fewer than 5 or, more preferably, fewer than 3. Most preferably, the cells are not passaged at all.

Alternatively, cells may be employed which are derived from an established cell culture line, either derived in a laboratory or purchased from commercial sources (e.g., ATTC, Rockville, Md.). Typically, such cell lines have lost some degree of differentiation and, therefore, they are generally not preferred. When established cell lines are employed, fetal cell lines or progenitor cell lines may be more desirable because such cells are generally more robust. These cells may also be grown in vitro in a standard cell growth medium until a suitable number or density of cells are obtained.

In another embodiment of the invention, cells are employed which have been genetically manipulated by the introduction of exogenous genetic sequences, or the inactivation or modification of endogenous sequences. Thus, for example, genes may be introduced to cause the cells to make proteins which are otherwise absent or defective in the host. Alternatively, production of scarce, but naturally occurring and desirable proteins, such as elastin, may be enhanced by appropriate genetic manipulations of the seeded cells. When implanted into a host, tissue-engineered constructs bearing such cells may serve as a production and delivery system for proteins which are otherwise absent, defective, or insufficient in the host. Thus, for example, genetically engineered endothelial cells that secrete tissue plasminogen activator have been seeded onto various synthetic grafts by Shayani and coworkers (Shayani et al. (1994)), and Chen (Chen et al. (1994)) has demonstrated the feasibility of adenovirus-mediated gene transfer into the endothelial cells of autologous vein grafts as a possible method to improve patency.

Alternatively, repression of gene expression may also be used to modify antigen expression on the surface of seeded cells and tissue constructs, thereby modifying the host's immune response so that cells are not recognized as foreign. Thus, for example, cells incapable of producing one or more MHC proteins, or incapable of loading MHC molecules with antigenic peptides, may be employed to reduce the likelihood of tissue rejection. In such cases, immunosuppression may not be needed when a non-autologous tissue-engineered construct is implanted into a host.

In accordance with the present invention, mammalian cells are seeded onto and within a porous substrate from a suspension so that, preferably, they are evenly distributed throughout the substrate at a relatively high density. Preferably, the cell suspensions comprise approximately $1 \times 10^4$ to $5 \times 10^7$ cells/ml of culture medium, preferably $2 \times 10^6$ to $2 \times 10^7$ cells/ml, and more preferably about $5 \times 10^6$ cells/ml. The optimal concentration of cells in a suspension may, of course, vary according to cell type, the propensity of the cells to form aggregates, the growth rate of the cell type, their binding affinity for the substrate used, and the substrate material used. The suspension may be formed in any physiologically acceptable fluid which does not damage the cells or impair their binding ability (e.g., a standard cell growth medium such as DMEM supplemented with 10% fetal bovine serum).

The cells may be seeded onto and within the porous substrate constructs of the invention by any standard method. For example, in one embodiment, the substrate is seeded by submersion into a cell suspension for a fixed period of time, and then the substrate is removed from the suspension and unbound cells are washed away. Alternatively, the substrate may be seeded with cells using a syringe or other sterile delivery apparatus. In a currently preferred embodiment, the cell suspension is dripped onto the substrate and subsequently the substrate is rotated in, for example, a rotating vessel. A tubular substrate, for example, as used in making a muscular, tubular tissue-engineered construct (e.g., a vascular construct), may be rotated about its lumenal axis during or after cell seeding to promote even distribution of the cells onto the surface of the substrate. After allowing a period of time for the cells to bind (optionally incubating the cell-seeded substrate in growth medium for a period), the cell-seeded substrate may be immersed in culture medium.

The "seeding time," or the time between initially contacting the mammalian cells with the substrate and later adding medium, may be varied significantly. Seeding times of one hour or more have been employed in the prior art. In the present invention, however, particularly when employing the hydrophilic, synthetic polymeric substrates described and disclosed herein, it has been found that substantially shorter seeding times, from 10–30 minutes or, more preferably, about 20 minutes, yield high densities of individually seeded cells with reduced formation of cell aggregates. This seeding time is to be distinguished from the "growth periods" discussed below.

As noted above, the substrates of the present invention may be seeded with suspensions comprising a multiplicity of cell types. Thus, for example, a mixture of two or more cell types (e.g., smooth muscle cells and fibroblasts, or smooth muscle cells and endothelial cells) may be seeded onto a substrate simultaneously, or one or more cell types can be seeded first, followed by seeding with one or more additional types before cell-seeded substrate is placed under suitable conditions for a growth period. In either case, this may be regarded as a single "seeding" although several cell types may be seeded in one or more steps. Thus, as used herein, a "primary cell-seeded construct" is a substrate which has been subjected to a first seeding with at least one cell type, but possibly more than one cell type, but which has not yet been maintained under suitable conditions for a growth period. During the first growth period, the cells of the primary cell-seeded construct grow and reproduce to yield a "primary tissue-engineered construct" in which the cells may or may not have yet reached confluence. This primary tissue-engineered construct may then be seeded a second time, again with one or more suspensions comprising one or more cell types, to form a "secondary cell-seeded construct." After maintaining the secondary cell-seeded construct under suitable conditions for a second growth period, during which the cells from the second seeding may grow and reproduce, the resulting construct is referred to herein as a "secondary tissue-engineered construct." Thus, for example, a vascular tissue-engineered construct may be produced by seeding smooth muscle cells onto the outer surface of a tubular porous substrate to form a primary cell-seeded construct which is maintained for a first growth period to form a primary tissue-engineered construct, and this construct may then be seeded with endothelial cells (and, optionally, fibroblasts) on the lumenal (and, optionally, outer) surface to form a secondary cell-seeded construct, which is maintained under suitable conditions for a second growth period to form a secondary tissue-engineered construct. Similarly, any number of additional constructs (tertiary, etc.) comprising various cell layers or admixtures, can be engineered according to the present invention (e.g., by inserting a vascular tissue-engineered construct into a larger substrate which is seeded with, for example, hepatocytes to form, ultimately, a vascularized liver tissue-engineered construct).

Suitable growth conditions and media for cells in culture are well known in the art. Cell culture media typically comprise essential nutrients, but also optionally include additional elements (e.g., growth factors, salts and minerals) which may be customized for the growth and differentiation of particular cell types. For example, "standard cell growth media" include Dulbecco's Modified Eagles Medium, low glucose (DMEM), with 110 mg/L pyruvate and glutamine, supplemented with 10–20% Fetal Bovine Serum (FBS) or 10–20% calf serum (CS) and 100 U/ml penicillin. Other standard media include Basal Medium Eagle, Minimal Essential Media, McCoy's 5A Medium, and the like, preferably supplemented as above (commercially available from, e.g., JRH Biosciences, Lenexa, Kans.; GIBCO, BRL, Grand Island, N.Y.; Sigma Chemical Co., St. Louis, Mo.).

For use in the methods of the present invention, several variations on standard cell growth media have been developed. In particular, when growing smooth muscle cells, it has been found that the inclusion of the streptomycin should be avoided, as this commonly used antibiotic tends to inhibit the development of the desired phenotype in response to externally applied physical forces, such as the pulsatile force of the invention. In addition, for growing any cells which normally produce a substantial collagenous extracellular matrix, an "enhanced cell growth medium" has been developed which comprises standard cell growth medium, as described above, supplemented with 1–10 mM, preferably 5 mM, HEPES buffer; 0.01–0.1 g/L, preferably 0.02–0.06 g/L, Vitamin C; 0.01–0.1 g/L, preferably 0.02–0.06 g/L, proline; 0.01–0.1 g/L, preferably 0.02–0.06 g/L, glycine; 0.01–0.1 g/L, preferably 0.02–0.06 g/L, alanine; and 0.5–5.0 $\mu$g/L, preferably 1.0–3.0 $\mu$g/L, of a copper salt (e.g., $CuSO_4$). Because Vitamin C has a half-life of only 6–8 hours at 37° C. in culture medium, Vitamin C is preferably replenished daily to enhance collagen synthesis by the cells. In addition, proline, glycine, and alanine are provided in excess to provide adequate amounts of these amino acids for the synthesis of collagen and other extracellular matrix proteins such as elastin. Copper ions are a necessary co-factor for elastin synthesis and, therefore, a source of copper ions (e.g., $CuSO_4$) is preferably included in media used to grow elastin-rich tissues. For the growth of endothelial cells, it is preferred that CS be used rather than FBS. In addition, growth factors, such as acidic fibroblast growth factor (aFGF), basic fibroblast growth factor (bFGF), platelet-derived growth factor (PDGF), transforming growth factor $\beta$ (TGF-$\beta$), or vascular endothelial cell derived growth factor (VEGF), may be employed at suitable concentrations (i.e., 1–10 ng/ml) to enhance cell growth or differentiation or the secretion of extracellular matrix proteins.

Cells are cultured under sterile conditions in an atmosphere of 5–15% or, preferably, 10% $CO_2$ and 90–100% or, preferably, 100% humidity in culture medium at or near the body temperature of the species of origin of the cells or the intended host (i.e., body temperature ±5° C., preferably ±2° C.). Thus, for example, human cells may be cultured at 32–43° C., more preferably 35–39° C., and most preferably 37° C. Cell viability may be determined by standard methods (e.g., trypan blue exclusion) known in the art, or by measuring cell attachment to, and the extent of proliferation on, the substrate. Quantitative assessment of in vitro cell attachment and viability may also be assessed using scanning electron microscopy, histology, and the incorporation of radioisotopes (e.g., $^3$H thymidine) according to art known methods.

To further enhance the attachment of cells to the substrate and/or to each other, various proteins or growth factors may be provided. For example, collagen, elastin, fibronectin, or laminin, may be provided to the substrate or to the growing constructs to promote cell adhesion. Thus, overlaying collagen on a material such as a polyanhydride substrate can increase adhesion of cells such as hepatocytes. Similarly, the substrate or construct can be impregnated with growth factors such as AFGF, bFGF, PDGF, TGF-$\beta$, VEGF, and various other angiogenic and/or other bioactive compounds that may be incorporated directly into the substrate or otherwise contacted with the growing cells (e.g., by addition to the cell culture medium). Multiple growth factors have been studied for their mitogenic effects on endothelial and smooth muscle cells (D'Amore and Smith (1993)). For example, aFGF, bFGF, PDGF have been found to stimulate smooth muscle cell proliferation, while bFGF and VEGF stimulate aortic endothelial cell growth. Basic FGF and VEGF have also been shown to bind to the subendothelial extracellular matrix and basement membrane, and are potent angiogenic factors (Edelman et al. (1991); Rogelj et al. (1989)).

D. Applying Pulsatile Stretch to Muscular Tissue Constructs

In another aspect of the present invention, a method for producing a muscular tissue-engineered construct is provided in which a distensible body is inserted within the lumen of a porous substrate to provide pulsatile stretch to seeded muscle cells. Thus, a substantially tubular porous substrate may be provided which defines a lumen, and a distensible tube is inserted within that lumen either before or after the porous substrate is seeded with muscle cells. While the muscle tissue is growing on and/or within the substrate, a pump in communication with the interior of the distensible body may then provide cyclic increases in pressure (e.g., by pumping a fluid or gas) to cause the distensible body to distend within the lumen of the porous substrate, contacting the inner surface of the substrate, and imparting a pulsatile stretching force to the substrate and growing muscle tissue. Without being bound to any particular theory of the invention, it is believed that this pulsatile stretch may enhance the orientation of the muscle cells into circumferential rings of muscle around the lumen, and may also enhance cell-cell adhesion, the formation of extracellular matrix, and the development and maintenance of an appropriate smooth muscle cell contractile phenotype.

In preferred embodiments for producing a vascular tissue construct, a distensible tube is distended in a cyclic manner which mimics a pulse of the organism from which the seeded cells are derived. The pulse rate may be chosen to mimic the pulse rate of the adult organism, or the higher pulse rate of the fetal organism. Thus, for example, a pulse rate of approximately 60–90/min, typically about 75/min, would mimic a resting pulse of a human adult. A pulse rate of approximately 140–160/min would mimic a human fetal pulse rate. In addition, higher pulse rates may be generally preferred as they may provide a greater stimulus for development of a contractile phenotype and mechanical strength in muscular tissue. In addition, for a vascular construct, the degree of pulsatile stretch induced in a cell-seeded construct or a tissue-engineered construct, as measured by the induced change in diameter of the construct, is preferably chosen so as to mimic that seen in a natural artery, but without applying excessive stretch which would disrupt the growing tissue. Thus, for example, after cell-seeding and during the early part of the growth period in which the cells are reaching confluence, a relatively low pulsatile stretch may be applied which causes the diameter of the construct to increase 2–10%, more preferably 2–6% with each pulse. Higher levels of pulsatile stretch at this early stage may disrupt or tear the tissue, and result in perforations in the vascular tissue construct. Later, after the cells have reached confluence, the tissue has thickened, and the construct has begun to assume an arterial histology (e.g., after 3–8 weeks), the cyclical increases in pressure within the distensible tube may be increased so that a pulsatile stretch of 6–10% or even 10–20% may be applied to the construct. As the pulsatile stretch seen in natural arteries varies from approximately 5% to approximately 20% (depending upon the diameter and location of the artery), it is expected that pulsatile stretches of 5–20%, or somewhat exceeding 20%, will be useful in producing vascular tissue constructs.

Similarly, the application of a pulsatile stretching force may be used in the production of other, non-vascular, but muscular, tubular tissue constructs. In each case, the diameter of the construct is chosen so as to approximate the diameter of the corresponding natural tissue or organ, and the pulsatile stretching force is chosen to approximate the corresponding natural forces. Thus, esophageal, intestinal or rectal tissue constructs may be produced in which the diameter of the construct approximates the diameter of a section of the esophagus, intestine or rectum, and in which the pulsatile force approximates the forces caused by peristaltic waves in a corresponding section of the alimentary canal. Alternatively, a ureteral or other muscular, tubular tissue construct may be produced in which the diameter of the construct and the pulsatile force approximates the corresponding natural diameters and forces. In the case of a bladder construct, a distensible body may be employed which approximates the shape of the lumen of the bladder, and pulsatile stretch may be applied which approximates the internal pressures experienced by a natural bladder (e.g., a urinary bladder, or gall bladder).

E. Applying Intralumenal Flow to Muscular, Tubular Tissue Constructs

Although the use of a distensible tube within the lumen of a growing muscular, tubular tissue construct is preferred in some embodiments, such a tube is not necessary to practice the present invention. Indeed, in order to better mimic the conditions of intralumenal flow and pulsatile force found in natural muscular, tubular structures, it may be preferred that a distensible tube is not employed. For example, after a suitable growth period, if the tissue forming the walls of a tubular construct has achieved sufficient strength and has formed a relatively fluid-tight seal around the lumen, culture medium may be pumped directly through the lumen (after removing the distensible tube, if present). Alternatively, if a substrate is employed, as described above, in which the inner surface is substantially less porous than the outer surface (e.g., having a void volume less than 25%, preferably less than 10%, and most preferably less than 5%), or in which a substantially non-porous film of substrate material is present on or adjacent to the inner surface, a distensible tube may not be needed, and fluid may be pumped directly through the lumen. Preferably, the inner surface is capable of resisting distension such that it increases in internal diameter by approximately 0.5–2.0%, preferably about 1.5%, per each 100 mm Hg of pressure applied internally.

In an alternative embodiment, a sheath or "sleeve" is provided which surrounds the exterior of the tissue construct to provide external mechanical support for the construct, and thereby prevent or inhibit disruption of the tissue by intralumenal flow and pressure, and/or prevent or impede fluid flow from the interior of the lumen through the walls of the construct. Such a sleeve may be porous or non-porous, distensible or rigid. Preferably, however, the sleeve comprises a distensible, non-porous material. In addition, it is preferred that the inner dimensions of the sleeve approximate the outer dimensions of the tissue construct such that the tissue construct contacts the inner surface of the sleeve during the application of intralumenal flow and/or pulsatile stretching force. The substrate may be placed within the sleeve prior to cell-seeding but, preferably, the substrate is placed within the sleeve after cell-seeding. Preferably, the sleeve is capable of resisting distension such that it increases in internal diameter by approximately 0.5–2.0%, preferably about 1.5%, per each 100 mm Hg of pressure applied internally.

Intralumenal fluid flow may begin at relatively low pressures and be increased as the tissue construct grows. Ultimately, it is preferred that the intraluminal flow be increased to levels which mimic or exceed the pressures and shear forces in the corresponding natural muscular structure. Thus, for example, internal pressures for arterial and venous vascular tissue constructs may be subjected to pressures of 60–150 mm Hg, 150–200 mm Hg, or even >300 mm Hg to mimic normal and/or elevated blood pressures although, as noted, lower pressures are advisable at the early stages of tissue growth to avoid disruption of the tissue. Similarly, vascular constructs may be subjected to shear forces of 5–30 dynes/cm$^2$, or even 30–60 dynes/cm$^2$, to mimic normal and/or elevated shear forces in the circulatory system, with lower levels preferably used initially.

As noted above, pulsatile stretching forces may also be included in the intralumenal flow. These forces may, for example, be employed to mimic the natural pulsing of blood circulating in arteries and veins; the peristaltic passage of food, chyme or feces through the alimentary canal; or the internal pressures of a filled bladder. As before, the pulsatile force may be relative low initially, with the force increasing to physiological levels as the tissue construct more fully develops.

F. Substrates for Use in Tissue-Engineering

In another aspect, the present invention provides substrates, including films and porous constructs, which are useful not only in tissue engineering, but also in tissue culture generally. As described above, these substrates may be formed of various biodegradable, biocompatible, synthetic polymeric materials (e.g., polyesters or polyanhydrides, optionally copolymerized with organic bases such as the basic amino acids), or proteinaceous polymers (e.g., collagen, elastin, fibronectin, laminin). Importantly, the substrates of the present invention are synthetic or proteinaceous polymers having hydrophilic surfaces which promote cell-seeding. Such hydrophilic surfaces may be produced by hydrolyzing the surface of the substrate material to create free hydrophilic groups on the surface, or by otherwise modifying the surface with acylating, sulfonating, glycosylating, or other conjugating groups to increase hydrophilicity and/or provide better cell-adhesion characteristics.

Thus, the substrate material may comprise a synthetic polymer with hydrolyzable bonds, such as polyesters or polyanhydrides, in which the surface of the substrate is hydrophilic. Preferred substrate materials include polyesters of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy hydroxy acids (e.g., $(COOH)(CH_2)_n(OH)$ or $(COOH)(CR_iR_j)_n(OH)$, where n is an integer between about 1 and 20, and each $R_i$ and $R_j$ is independently selected from the group consisting of —H, —OH, —SH, —NH$_2$, the halogens, the side chains of the naturally occurring amino acids, and any straight chain or branched, substituted or unsubstituted, saturated or unsaturated, low molecular weight (e.g., $C_1$–$C_{14}$) alkanyl, haloalkyl, thioalkyl, aminoalkyl, aryl, aralkyl, alkenyl, aralkenyl, heteroaryl, or alkoxy group, or a secondary or tertiary amine substituted with such groups) or polyanhydrides of straight chain or branched, substituted or unsubstituted, saturated or unsaturated, linear or crosslinked, alkanyl, haloalkyl, thioalkyl, aminoalkyl, aryl, aralkyl, alkenyl, aralkenyl, heteroaryl, or alkoxy dicarboxylic acids (e.g., $(COOH)(CH_2)_n(COOH)$ or $(COOH)(CR_iR_j)_n(COOH)$, where n is an integer between about 1 and 20, and each $R_i$ and $R_j$ is independently selected from the group consisting of —H, —OH, —SH, —NH$_2$, the halogens, the side chains of the naturally occurring amino acids, and any straight chain or branched, substituted or unsubstituted, saturated or unsaturated, low molecular weight (e.g., $C_1$–$C_{14}$) alkanyl, haloalkyl, thioalkyl, aminoalkyl, aryl, aralkyl, alkenyl, aralkenyl, heteroaryl, or alkoxy group, or a secondary or tertiary amine substituted with such groups). Polymers including mixtures of ester and anhydride bonds (e.g., copolymers of glycolic and sebacic acid) may also be employed. Thus, for example, preferred substrate materials include polyglycolic acid polymers (PGA), polylactic acid polymers (PLA), polysebacic acid polymers (PSA), poly(lactic-co-glycolic) acid copolymers (PLGA), poly(lactic-co-sebacic) acid copolymers (PLSA), poly(glycolic-co-sebacic) acid copolymers (PGSA), etc.

Although the manner in which the hydrophilic surface is produced is irrelevant to the present invention, such surfaces may conveniently be formed by hydrolysis with bases (e.g., NaOH, KOH, LiOH), acids (e.g., $H_2SO_4$, trifluoro-acetic acid (TFA), HCl, HF), catalysts (e.g., imidazoles, glycolytic enzymes) or other methods (e.g., plasma treatment). In a presently preferred embodiment, a polyester (e.g., PGA, PLA, PGLA) or polyanhydride (e.g., PSA) or mixed polyester-polyanhydride, is briefly treated with an alkaline solution (e.g., 1 N NaOH for 1 minute) to hydrolyze ester and/or anhydride bonds at the surface, thereby creating free carboxyl and/or hydroxyl groups on the surface. Very brief treatments, or treatments with weak bases, acids or catalysts, leads to only partial hydrolysis of the surface (i.e., surface accessible ester and anhydride bonds remain). Longer or more vigorous treatments lead to greater hydrolysis of surface accessible ester and anhydride bonds, and some dissolution such that the substrate, whether a film or a fiber, becomes thinner. At some point, an equilibrium is reached, in which further hydrolysis causes free monomer (or small polymer) units to be formed which diffuse away into the solution while exposing previously surface-inaccessible ester and/or anhydride bonds. After this equilibrium point is reached, further treatment does not result in increased hydrophilicity but, rather, leads to continued dissolution and thinning of the substrate. For example, using a PGA fiber having a diameter of 13 μm, after approximately 1 minute in 1 N NaOH solution, up to 10% of the repeating unit of the polymer had been hydrolyzed on the surface, causing a decrease in fiber diameter of about 0.65 μm or less.

In accordance with the present invention, the hydrophilic surface which is produced on a synthetic polymer substrate may be characterized in several ways. In one preferred embodiment, the hydrophilicity is defined by the contact angle of the substrate as measured by the sessile drop technique (see, e.g., Adamson, ed. (1990) *Physical Chemistry of Surfaces*, 5th Edition, John Wiley & Sons, Inc., New York, pp. 379–420). In the case of a film, the contact angle may be measured directly. In the case of a fiber, the contact angle may be measured using a similarly-treated film of the same material (i.e., the contact angle of a PGA fiber treated in 1 N NaOH for 1 minute is assumed to be the same as the contact angle of a PGA film treated for 1 minute in 1 N NaOH). In preferred embodiments, the substrate displays a contact angle with water of less than 45°, more preferably less than 20° or 10°, and most preferably less than 5°.

Alternatively, the hydrophilicity of the substrates of the present invention may be defined by the density of hydrophilic groups on the surface. Many techniques are known in the art for conducting such measurements. In one preferred embodiment, the surface density of hydrophilic functional groups can be determined using X-ray photoelectron spectroscopy (XPS). Using a PGA film, for example, surface hydrolysis will increase the ratio of oxygen to carbon from 1:1 in the polyester to 1.5:1 in a theoretically completely hydrolyzed surface. Thus, by using XPS, one can estimate the fraction of bonds which have been hydrolyzed by calculating the ratio of oxygen to carbon atoms at the surface. Less preferred (because the measurements may extend below the surface of the substrate) are nuclear magnetic resonance (NMR) techniques which can distinguish between different bond types (e.g., ester versus hydroxyl and carboxyl). In addition, many other techniques are known in the art, including those which first derivatize the surface functional groups for ease of measurement, and these may also be employed. Irrespective of the means which are employed for determining the hydrophilicity of the surface, preferred surfaces for the present invention have a density of hydrophilic groups (e.g., carboxyl, hydroxyl, thiol, amine, sulfonyl, guanidine, amide) approximately 5–20 pmol/cm$^2$, more preferably approximately 10 pmol/cm$^2$. Thus, for example, a fibrous PGA substrate subjected to 1 N NaOH for 1 minute was found by XPS to have a surface density of hydroxyl and carboxyl groups of about 10 pmol/cm$^2$, representing hydrolysis of approximately 10% of the surface accessible ester bonds.

As an alternative to synthetic polymer substrates, porous substrates may be employed which comprise proteinaceous polymers. Such substrates are known in the art and have been used in the production of tissue-engineered constructs. For example, collagen gels have been used to produce vascular tissue constructs (Weinberg and Bell, (1986)), and collagen sponges and meshes are now commercially available (e.g., from Ortec International, Inc., New York, N.Y.). Such collagenous substrates, as well as similarly constructed substrates based on elastin, fibronectin, laminin, or other extracellular matrix or fibrillar proteins, may be employed in the methods and constructs of the present invention. Such proteinaceous polymer substrates may be in the form of fibrous meshes, as described above, or may be in the form of non-fibrous substrates such as sheets, films, or sponges. In addition, these substrates may include proteinaceous polymers which have been modified by, for example, acylating, sulfonating, glycosylating, or otherwise conjugating reactive groups of the amino acid side chains with other moieties to increase hydrophilicity and/or provide better cell-adhesion characteristics. For example, the proteins may be acylated with dicarboxylic acid anhydrides to increase hydrophilicity, or may be conjugated to cell-adhesion peptides to increase the density or avidity of cell-seeding. Such proteinaceous polymers have the advantage that they are completely biological in nature and, therefore, will have reduced immunogenicity if syngeneic to the host.

In one set of preferred embodiments, a porous substrate for use in tissue culture (including tissue engineering) comprises a biocompatible, synthetic or proteinaceous polymer material, as described above, and is further characterized by a void volume of greater than 90%, preferably greater than 95%, and most preferably greater than 97%.

In some embodiments, a porous substrate for use in tissue culture (including tissue engineering) comprises a porous mesh of biocompatible, synthetic or proteinaceous polymer fibers having diameters of between approximately 5–20 $\mu$m, preferably approximately 10–15 $\mu$m. In a related embodiment, the porous substrate comprises a porous mesh of fibers in which substantially parallel fibers are separated by approximately 20–200 $\mu$m, preferably approximately 50–100 $\mu$m. Similarly, a porous substrate is provided in which the substrate has an average pore size of less than 200 $\mu$m, preferably less than 175 $\mu$m, and most preferably less than 150 $\mu$m.

In some embodiments, a porous substrate for use in tissue culture (including tissue engineering) comprises a porous mesh of biocompatible, synthetic or proteinaceous polymer fibers having a surface area per unit weight of approximately 1–5 cm$^2$/mg, preferably about 1–3 cm$^2$/mg, and most preferably about 2 cm$^2$/mg. Thus, for example, PGA fibers having diameters of 5, 13 and 20 $\mu$m have surface areas per unit weight of approximately 5.2, 2.0 and 1.3 cm$^2$/mg, respectively. In addition, given a density of substrate material of approximately 1.5 g/cm$^3$ (for PGA and similar polymers), and a preferred void volume for a fibrous mesh of approximately 90–97%, the density of the mesh is preferably about 0.15–0.045 g/cm$^3$. Therefore, for fibers having diameters of 5–20 $\mu$m, and surface area per unit weight of 1–5 cm$^2$/mg, the surface area per unit volume is approximately 45–750 cm$^2$/cm$^3$, preferably about 75–250, and most preferably about 150 cm$^2$/cm$^3$.

G. Muscular, Tubular Tissue Constructs with Physiological Strengths

In another aspect, the present invention provides muscular, tubular tissue-engineered constructs, including vascular constructs, which may be used medically as prosthesis for the repair or replacement of damaged natural structures, or which may be used for in vivo or in vitro tests as models of natural structures. Significantly, the muscular, tubular tissue constructs of the present invention have significantly higher cell density and significantly higher strength than the prior art constructs. Thus, for example, the present invention provides a tissue-engineered muscular, tubular vascular construct of living mammalian tissue defining a tubular structure with walls and a lumen passing therethrough. In the construct, smooth muscle cells are oriented circumferentially, or in rings, around the lumen. It is believed that the application of pulsatile stretching forces during the growth of the tissue construct greatly enhances the ability of the smooth muscle cells to orient circumferentially (in opposition to the pulsatile force) and to maintain a contractile phenotype.

In preferred embodiments, the cell density of smooth muscle cells within the walls of the construct is at least 10$^7$ cells/cc, preferably at least 10$^8$ cells/cc, and most preferably about 3×10$^8$ cells/cc. Densities up to 10$^9$ cells/cc may also be employed. It is believed that the use of porous substrates with large void volumes and hydrophilic surfaces greatly enhances the initial seeding density of cells on primary cell-seeded constructs, and that this initially higher density leads to a higher final density. It is also believed that the use of an enhanced growth medium, as described herein, rich in Vitamin C, copper ions, and certain amino acids, greatly enhances the ability of the cells to develop into a dense tissue and to deposit a strong extracellular matrix.

In preferred embodiments, the tubular construct is capable of withstanding an internal, sustained (e.g., for at least 1 hour, but preferably several weeks) or pulsatile pressure of at least 100 mm Hg, preferably at least 110 mm Hg, and most preferably, at least 120 mm Hg, without rupturing (i.e., tearing of the walls resulting in macroscopic perforations and fluid leakage from the lumen). Employing the methods of the present invention, muscular tubular constructs have been produced which are capable of withstanding >2,000 mm HG for sustained periods, but constructs capable of withstanding at least 130–150 mm Hg, preferably at least 150–175 mm Hg, and more preferably at least 175–200 mm Hg of internal pressure without rupturing will have utility in many applications. It is believed that the application of pulsatile stretching forces during the growth of the construct, in combination with the hydrophilic substrates, large void volumes, higher seeding densities and/or enhanced growth medium, permits the production of the high strength muscular, tubular tissue constructs of the present invention.

Similarly, in preferred embodiments, the muscular, tubular construct is capable of withstanding internal, sustained or pulsatile shear forces of at least 5–10 dynes/cm$^2$, preferably at least 10–20 dynes/cm$^2$, and most preferably at least 20–30 dynes/cm$^2$, without rupturing. It is contemplated that muscular, tubular constructs resisting shear forces as high as 30–60 dynes/cm$^2$ may be produced according to the presently disclosed methods. Again, it is believed that the application of pulsatile stretching forces during the growth of the construct, in combination with the hydrophilic substrates, large void volumes, higher seeding densities and/or enhanced growth medium, permits the production of the high strength muscular, tubular tissue constructs of the present invention.

Further, in preferred embodiments, the muscular, tubular construct is capable of retaining sutures of 4-0 size that are sewn 1 mm from the cut edge of the construct with a force of greater than 50 grams, more preferably with a force of greater than 75 grams, and most preferably with a force greater than 100 grams. It is contemplated that muscular, tubular constructs with these suture retention strengths may be produced according to the presently disclosed methods.

Further, in preferred embodiments, the muscular, tubular constructs demonstrates static and dynamic compliances which are comparable to those observed for the corresponding native tissue. For native blood vessels, static and dynamic compliances are in the range of 2–25% change in diameter over a pressure range of 100 mm Hg. Thus, static an dynamic compliances for the constructs in the range of 2–25% change in diameter over a pressure range of 100 mm Hg, and most preferably 2–10% change in diameter over a pressure range of 100 mm Hg, may be produced according to the presently disclosed methods.

Further, in preferred embodiments, the muscular, tubular construct demonstrates cell densities per cubic cm that are comparable to native tissues. For native blood vessels, cell densities are reported in the range of 1–3×10$^8$ cell/ml. Thus, muscular, tubular constructs with observed cell densities of greater than 1×10$^7$ cells/ml, or more preferably of greater than $5 \times 10^7$ cells/ml, or most preferably greater than $1 \times 10^8$ cells/ml, may be produced according to the presently disclosed methods.

The vascular tissue-engineered constructs of the invention may be distinguished from naturally occurring arteries by at least one of the following characteristics: (1) they are produced from cultured cells grown in vitro; (2) they may contain residual substrate material interspersed with the tissue; (3) they may lack an adventitia; (4) they may lack an intermediate layer of the intima; (5) they may lack the internal elastic lamina of the intima; (6) they may lack fibroblasts in the intima; and (7) they may lack fibroblasts in the medial layer.

EXAMPLES

Preparation of Polymeric Substrates for Cell Growth

A textile process was developed by the Langer laboratory at MIT and Albany International Research Company (Mansfield, Mass.) to produce a non-woven mesh out of fine PGA fibers. The unprocessed PGA has a weight average molecular weight ($M_w$) of 68.9 kD and a number average molecular weight ($M_n$) of 25.1 kD, as measured by gel permeation chromatography (Freed et al. (1994)). The mesh is formed from a multifilament yarn that is produced by polymer extrusion, with a tenacity of 4.5–5.3 grams per denier. The yarn is crimped, cut, carded into a lofty web, and needled to form a nonwoven mesh using barbed needles. Heat setting further increases the dimensional stability of the mesh. The mesh has a 97% void volume and a thickness ranging from 0.5 to 1.0 millimeters. The individual PGA fibers in the mesh are approximately 13 microns in diameter and are separated by distances of 50–100 microns. In vitro studies have demonstrated that this mesh degrades to approximately 30% of its original mass over eight weeks in tissue culture conditions.

Polyglycolic acid (available commercially in pellets from Birmingham Polymers, Incorporated, Birmingham, Ala.) may be cast into flexible films of 10–50 microns thickness by either heating above the melting point in pressurized platens, or by solvent casting from a solution in hexafluoroisopropanol. PGA films provide a good surface for the attachment and growth of both endothelial cells and smooth muscle cells.

Preparation of a Porous Substrate with a Hydrophilic Surface

A porous substrate with a hydrophilic surface is prepared from polyglycolic acid (PGA) mesh (Albany International Research Co, Mansfield, Mass.) by modifying the surface chemistry to increase hydrophilicity. The modified surface chemistry greatly enhances the wettability of the substrate, and greatly improves the number of cells which may be deposited on the surface during seeding. The PGA substrate material is treated as follows:

Wash PGA mesh in hexane for 30 minutes.

Wash in dichloromethane for 30 minutes.

Wash in diethyl ether for 30 minutes.

Lyophilize PGA mesh overnight to remove all traces of organic solvents.

Place PGA mesh in ethanol.

Remove PGA mesh to distilled water.

Remove PGA mesh to a 1.0 normal solution of NaOH, use tweezer to agitate the mesh, keep in NaOH solution for 1.0 minutes.

Remove to distilled water, use tweezer to agitate, to wash out base solution.

Repeat washes in distilled water until the wash solution remains at pH 7.0.

Lyophilize overnight to dry, and then assemble into tubular substrate in the bioreactor system.

In one set of experiments in which smooth muscle cells were seeded onto modified or unmodified PGA mesh, the seeding density of the smooth muscle cells was $3.0 \times 10^5$ cells/mg of modified PGA mesh. Unmodified PGA substrate (i.e., not hydrolyzed to increase hydrophilicity) was capable of binding only half as many cells under identical seeding conditions. Scanning electron microscopy analyses of the smooth muscle cells on the PGA substrates showed that the cells were attached and spread out on the surface. On partially hydrolyzed PGA substrates, cells were present both as cell aggregates and individual cells. Conversely, the cells on the surface of unmodified PGA substrates existed primarily as cell aggregates. These results indicated that the surface hydrolyzed PGA substrates attached more cells than the unmodified PGA substrates.

Figure 4:
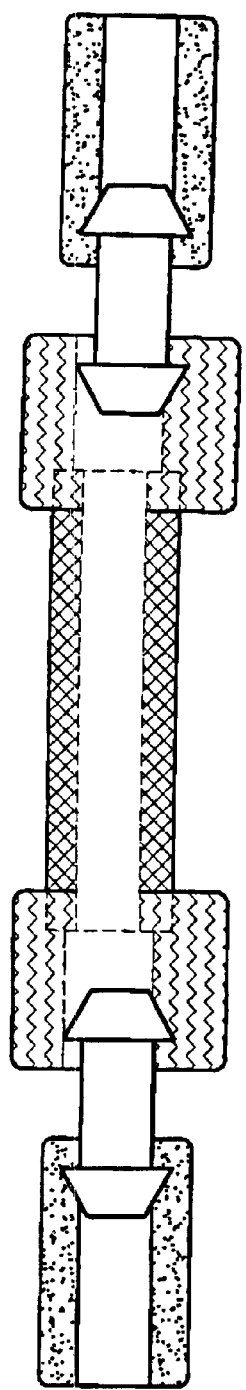
FIG. 4 shows a compound construct (40) comprising a first tubular construct (20) joined to two cuffs (30), which may be joined by connectors (50) to tubing (60) leading to a bioreactor flow system.

Preparation of a Porous Substrate for a Vascular Tissue-Engineered Construct Surface-modified PGA mesh is rolled into tubes with inner diameters of approximately 3–6 mm. The lengths of the tubes are on the order of 1–10 cm. The tubes are sewn together with uncoated PGA suture (Davis & Geck, Inc., Manati, P. R.). The ends of these tubular porous substrates are then sewn to porous Dacron vascular grafts having approximately 5 mm internal diameters (Bard Vascular Systems Division, Haverhill, Mass.), using uncoated Dacron suture (Sherwood-Davis & Geck, St. Louis, Mo.). The Dacron graft at the ends of the tubular porous substrate is also seeded with smooth muscle cells during the cell-seeding process, described below. The purpose of the Dacron graft is to provide a non-degradable interface between the degradable porous substrate and the plastic and glass of the flow system. The porosity of the Dacron allows dense incorporation of smooth muscle cells into the Dacron graft, thus forming a fluid-tight seal between the engineered tissue and the rest of the bioreactor's flow system. Referring to FIG. 4, the tubular porous substrate (20) is sutured to the Dacron grafts (30) to form the compound construct (40). The non-degradable Dacron graft is sutured to plastic connectors (50) on either end of the substrate using uncoated Dacron suture.

Plastic connectors (50) with Pharmed tubing (60) are assembled on either end of the Dacron grafts. All of these connections are made such that the inner lumen of all the various tubings is approximately the same (e.g., 3–6 mm), to minimize turbulence when fluid flow is applied to the inner lumen of the tissue-engineered construct. However, for the first growth period, it is not recommended to apply flow directly through the inside of the porous substrate because the application of flow and pressure to the lumen of the substrate may result in leakage through the substrate and disruption of the adherence and confluence of the tissue growing thereon. Rather, for the first growth period, a highly distensible silicone tube (Patter Products, Beaverton, Mich.) is inserted through the lumen of the substrate and the various connectors. Application of a pressure of approximately 300 mm Hg to the interior of the tube results in an increase in outer diameter of approximately 5%. By placing the distensible tube within the lumen of the substrate, it is possible to apply a known pulsatile circumferential stretch to the tissue-engineered construct during the first growth period.

Bioreactors for Tissue-Engineered Constructs

The porous substrate construct of the present invention may be placed within a glass bioreactor for cell-seeding and tissue growth. Bioreactors are made entirely of glass and are individually blown, having a volume of approximately 200 cc. A small stir bar is added to each bioreactor. For use in producing vascular tissue-engineered constructs, bioreactors are produced with inner glass connector arms for attachment to the connectors and distensible silicone tubes described above. Glass connector arms on each end of the bioreactor have inner diameters of, for example, 3 mm and outer diameters of, for example, 5 mm. The entire bioreactor reactor assemblies are sterilized with ethylene oxide, and allowed to out-gas for a minimum of 3 days, to remove any residual cytotoxic ethylene oxide gas. The porous substrates are placed within the bioreactors and cell-seeded. After seeding, the bioreactors are placed in a standard tissue culture incubator for the time required to assemble the remaining components of the system.

Major components of the flow system for a vascular tissue-engineered construct (with distensible tube for applying pulsatile stretch) are as follows:

Pharmed tubing, 1/8" (3.1 mm) inner diameter (PGC Scientifics, Gaithersburg, Md.)

Bel-O-Just pulsatile piston pump (Gorman-Rupp Industries, Bellville, OHio)

Pulse dampener (compliance chamber) (Cole-Parmer Instrument Co, Niles, Ill.)

Tissue culture flask, which functions as a gas-permeable, flexible fluid reservoir for the flow system (Baxter)

Pressure transducer (Argon Medical, Texas)

Pressure display monitor (Hewlett-Packard, Texas)

Under sterile conditions, Pharmed tubing is connected to the fluid reservoir, compliance chamber, and the pressure transducer. The fluid reservoir is filled with PBS to which antibiotics are is added (as a precaution, in case the flow system leaks). The flow system assembly and four bioreactors were then placed in a glovebox incubator. The glovebox system is designed to function as a tissue culture incubator, with controlled temperature, humidification, and gas atmosphere. However, the glovebox is also an airtight system, which is sterilizable, and which can be accessed with a minimal introduction of contaminating outside atmosphere. The glovebox assembly is particularly important in view of the fact that the medium in which the tissues are cultured contained a minimum of added antibiotics.

Major components of the glovebox incubator are as follows:

Acrylic glovebox (PGC Scientifics, Gaithersburg, Md.)

Digital Proportional temperature controller (Cole-Parmer Instruments, Niles, Ill.)

Cast-aluminum hot plate (Cole-Parmer, Niles, Ill.)

Germicidal UV lamp (PGC Scientifics, Gaithersburg, Md.)

Direct-reading gas flow meter (Cole-Parmer, Niles, Ill.)

Four-position magnetic stirrer (Bellco Glass, Vineland, N.J.)

The bioreactors are attached to the flow system inside the glovebox in a sterile fashion. The Pharmed tubing is attached to the pulsatile piston pump outside the glovebox, and pulsatile perfusion of the four bioreactors is initiated. Pressure in the system is monitored continuously, using a pressure transducer that is in contact with the pumped fluid. The atmosphere in the glovebox is maintained at 100% humidity using a pan of water with a large surface area. $CO_2$ concentration is maintained at 10%, with a balance of room air. The gas flow rates to the glovebox are adjusted in order to provide adequate gas turnover and oxygen supply to the cultured tissues. Glovebox temperature is maintained at 37° C. The glovebox is accessed only as required for sampling and medium changes, and is re-sterilized after each access using the germicidal UV lamp.

Preparation of Primary Vascular Tissue Constructs

Cells for a vascular tissue-engineered construct are sourced from explants of bovine thoracic aorta obtained from a local abattoir on ice. Aortas are placed in phosphate buffered saline (PBS) supplemented with penicillin and streptomycin (Pen/Strep). Aortas are incised longitudinally, and the inner surface (endothelial surface) is washed with copious amounts of PBS with antibiotics, in order to reduce the incidence of bacterial contamination, and also to reduce the chance of fibroblast contamination. Endothelial cells are obtained by scraping the lumenal surface with a scalpel blade, and rinsing the cells into tissue culture flasks containing DMEM with 10% calf serum.

Smooth muscle cells are obtained from the medial layer of calf thoracic aortas in the following fashion: the intimal layer of the aorta is stripped away with forceps, and the outer adventitia is removed along with the outer media. The remaining middle portion of the media is then laid down in a petri dish, with the previously-endothelial side down, and the tissue is scored at one centimeter intervals. Sufficient DMEM with Pen/Strep and 15% FBS is then added to cover the bottom of the dish, without causing the tissues to float above the surface. Tissues are cultured for seven to ten days, and smooth muscle cells migrate off the tissues to form a confluent monolayer in the dish at the end of that culture period. The tissues are removed after seven to ten days, and the cells cultured for a total of 2–3 passages. Smooth muscle cell identity and purity are confirmed by visual appearance and by immunostaining for smooth muscle α-actin. Cells are cryopreserved until needed for use in tissue-engineered vessels.

Smooth muscle cells are brought up from cryopreservation and grown in DMEM with 15% FBS. Smooth muscle cells are routinely used before passage 5, and preferably are used at least before passage 10. In addition, the cells are also preferably shown to be mycoplasma-free. The smooth muscle cells are removed from confluent or sub-confluent culture by trypsinization (0.05% trypsin, 0.02% EDTA), centrifuged to a pellet and gently re-suspended to a single cell suspension in 1–2 ml of fresh standard cell growth medium, for a cell concentration of approximately $2-5\times10^6$ cell/ml.

Substrate films and three-dimensional porous substrates of PGA are sterilized with ethylene oxide gas and out-gassed for a period of at least three days prior to seeding. The re-suspended cells are pipetted onto the polymeric substrate ((preferably pre-wetted if not sufficiently hydrophilic) and allowed to attach over at least 15 minutes, preferably about 30 minutes, and then additional fresh medium is added to the culture. The substrate is rotated at the speed of 0.66 rpm in 10% $CO_2$ at 37° C. to evenly distribute the cells onto the substrate.

Preparation of Secondary Vascular Tissue Constructs

Bovine aortic endothelial cells are isolated from aortae prepared as described above. Briefly, the intima of bovine aorta is isolated by scraping with a scalpel blade and digesting the cell layer with 0.1% collagenase/0.1% soybean trypsin inhibitor/0.5% BSA-Fraction V (Worthington Biochemical Co., Freehold, N.J., and Integren Co., Purchase, NY) for 15 minutes to separate the cells. The cells are then spun down, resuspended in DMEM (Gibco, Grand Island, N.Y.) with Pen/Strep and 10% CS, and cultured for a total of 2–3 passages. Endothelial cell identity and purity are confirmed by visual appearance and by immunostaining for von Willebrand factor. Cells are cryopreserved until needed for use.

Endothelial cells are brought up from cryopreservation and the cells are grown in DMEM, supplemented with 10% CS (Sterile Systems, Logan, Utah), L-glutamine, and penicillin 10,000 U/ml, until they reach sub-confluence. The endothelial cells are trypsinized, spun down, and re-suspended to a single cell concentration of $1-5 \times 10^6$ cells/cc.

To seed the endothelial cells onto a tubular primary vascular tissue construct, already bearing growing smooth muscle tissue, the bioreactor is disconnected from the pulsatile flow system in sterile fashion. The bioreactor is removed to a tissue culture hood, and the medium is drained. Preferably, to enhance endothelial cell binding, a protein solution containing either fibronectin, collagen type IV, laminin, or a mixed gel of basement membrane proteins (all from Sigma Biosciences, St. Louis, Mo.) is pipetted onto the inner and outer surfaces of the smooth muscle cell tube. The bioreactor is placed on a bottle roller or other rotational device and rotated for 20–30 minutes in the tissue incubator, and then returned to the tissue culture hood. The construct is again removed from the incubator, drained, and one end of the primary tissue construct is occluded and the endothelial cell suspension is injected through the other end into the lumen of the tube. Cells are also seeded onto the outer surface of the construct. The tubular construct is then sealed and slowly rotated over at least 30 minutes, preferably 1–12 hours, or for a time sufficient to allow optimal cell seeding. The lumen is then gently rinsed and the secondary cell-seeded construct is returned to culture with culture medium in incubators at 37° C. with a 10% $CO_2$ atmosphere.

Culturing a Tubular Construct with Pulsatile Stretching

Figure 5:
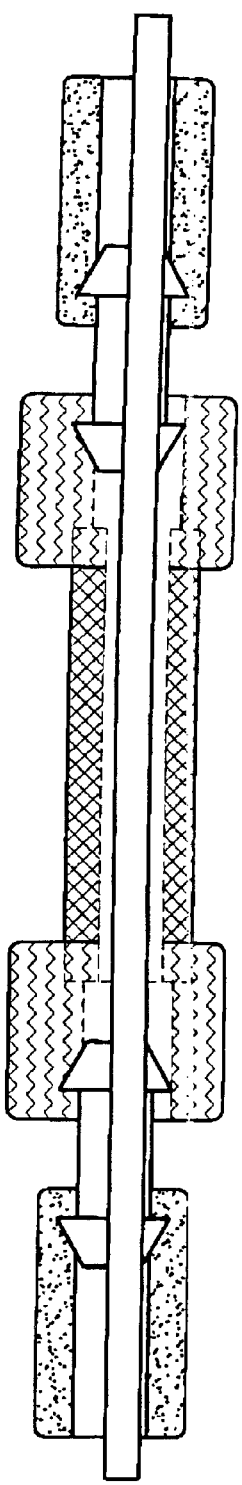
FIG. 5 shows a compound construct (40) comprising a first tubular construct (20) joined to two cuffs (30), and further joined by connectors (50) to the tubing (60) of a bioreactor flow system. A distensible tube (70) is inserted within the lumen of the compound construct (40) to apply pulsatile stretching force to the construct.

A pulsatile flow system was developed for use in producing muscular, tubular tissue-engineered constructs. A flexible, distensible tube made, for example, of silicone is inserted into the lumen of a tubular porous substrate preferably before or, optionally, after the substrate has been seeded with smooth muscle and/or endothelial cells. For this purpose, a silicone tube was manufactured having an inner diameter of 0.109 inches, an outer diameter of 0.125 inches, and a wall thickness of 0.008 inches, and which increased approximately 1.5% in outer diameter for each 100 mm Hg of pressure applied internally. Thus, referring to FIG. 5, a distensible tube (70) is inserted within the lumen of a compound construct (40), passing through the connectors (50) and tubing (60), and is connected to a pump circuit. The cell-seeded constructs with the distensible tube are maintained in culture medium (or "enhanced" medium) in a bioreactor. Pressure is applied to the lumen of the tubular constructs in a continuous or pulsatile fashion by causing the distensible tube to distend under pressure from within. Initially, pressures are chosen such that the lumen of the construct is distended only 4–6% in diameter. Over a period of weeks, as the cells replicate and the constructs become stronger, the pressures and flows applied to the vessels may be gradually increased to the appropriate physiologic range. Rates of flow and pressure increase are adjusted to maximize the transmural and shear forces applied to the vessel without causing gross structural damage to the tissue. Using such silicone distensible tubes, cyclic pressures of 270/−31 mm Hg (i.e., the "diastolic" pressure being negative) have been useful in growing bovine and porcine vascular tissue constructs.

Growth Culture Maintenance

During the weeks-long culture period needed for producing tissue-engineered constructs, the medium in each bioreactor is preferably replenished (50% volume) twice per week. Thus, an equivalent complete volume of fresh medium is supplied each week. Each day, Vitamin C which is freshly reconstituted from the dry form is added to each bioreactor. After a period of two to four weeks, the FBS content of the enhanced medium is decreased from 15% to 5%, in order to stimulate differentiated function and a contractile phenotype of the smooth muscle cells. Other additives in the enhanced medium recipe remain the same.

Measurement of Burst Strengths and Compliances

Muscular, tubular engineered constructs are harvested from bioreactors after an appropriate culture period of, for example, eight weeks, and are attached to a perfusion system which provides static or dynamic pressures directly to the lumen of the vessel, without an interposed silicone tube. Static pressures of up to 300 mm Hg are applied in static fashion manually with a syringe, and pulsatile pressures up to 300/200 mm Hg at a pulse rate of 60–165 beats per minute. Using this method, static and dynamic compliances have been measured in the range of 2–25% change in initial outer diameter over pressure ranges of 100 mm Hg. After measurement of compliances, the burst strength of the tubular construct is determined by applying increasing static pressures to the lumen of the construct manually using a syringe, in increments of 1.0 psi (approximately 50 mm Hg), until the vessel tears or ruptures. The measured rupture strengths of the constructs are in the range of 600–2,800 mm Hg, and vary with the conditions under which the construct is cultured.

Suture Retention Strength

Tubular engineered constructed are secured using a suture tie to a stopcock, which is in turn fastened to a syringe pump. The syringe pump is set to withdraw the engineered construct from a calibrated force transducer at a known rate of speed, less than 1 mm per second. A silk suture, 4-0 preferably, is threaded through one wall of the construct at a distance of 1 mm from the cut end of the construct. The 4-0 suture is attached to the calibrated force transducer, and the syringe pump then withdraws the construct away from the transducer until the suture tears out of the tubular construct. The measured force exerted on the 4-0 suture is monitored continuously, and the force at which the suture tears out is the suture retention strength. Using this technique, we have measured suture retention strengths for tubular constructs of 30–150 grams, depending on the culture conditions used to grow the construct.

Measurement of Cell Density

Tubular engineered constructs are harvested from bioreactors and are rinsed with phosphate buffered saline (PBS). After excess PBS buffer was removed, the accurate weight of the wet tissue was measured (~10 mg). The tissue was placed in a cryovial (2 ml) and lyophilized. The dry weight of the tissue was measured. The tissue was digested in a papain solution containing 25 µl papain (Sigma, 28 mg/ml), 50 µl EDTA (stock 0.5M to final 5 mM), 4.4 cysteine HCl (5 mM) in 5 ml PBS at 60° C. water bath overnight until most of the tissue was dissolved. The solution was cooled to room temperature and sonicated for 30 seconds. The DNA content was determined by measuring the fluorescence intensity of a dye (Hoechst 33258) upon binding to DNA ($l_{ex}$=365 nm, $l_{em}$=458 nm). Calf thymus (10 µg/ml) was used as a DNA standard. The number of cells was calculated based on a constant of 8.5 pg DNA/smooth muscle cell. Using this technique, cell densities of tubular engineered constructs have been measured in the range of $8-14 \times 10^7$ cells/ml, depending on the culture conditions used to grow the vessel.

Pharmacologic Reactivity of Functional Vessels

Segments of neo-artery three mm in length were assessed for reactivity to pharmacologic agents using techniques previously reported. Briefly, segments were placed in physiological saline bubbled with 95% $O_2$ and 5% $CO_2$, and mounted on tungsten wires in conventional myographs connected to a pen recorder. Freshly excised segments of rabbit abdominal aorta were used as controls. Vessels were maintained at a resting tension of four grams for 30 minutes prior to testing. Vessels were exposed to indomethacin $10^{-5}$ M, LNNA $10^{-4}$ M, norepinephrine $10^{-6}$ M, prostaglandin $F_{2\alpha} 10^{-5}$ to $10^{-4}$ M, papavarine $10^{-6}$ to $10^{-5}$ M, serotonin $10^{-6}$ to $10^{-5}$ M, endothelin-1 $10^{-7}$ and potassium 30–60 mM. Vessel segment showed reproducible constriction to prostaglandin $F_{2\alpha}$, serotonin, and endothelin-1, as well as relaxation to papavarine. In some experiments, the magnitude of the constriction response was augmented by prior exposure to indomethacin. Magnitude of constriction was on the order of 5–10% of control values, but the presence of reactivity demonstrates the presence of a functional, muscular tissue.

REFERENCES

Barrera et al. (1993)*J. Am. Chem. Soc.* 115:11010–11011.
Bell (1994) Jour. Cellular Biochem. 56, 147–149.
Cao et al. (1994) Transplantation Proc. 26(6), 3390–3391.
Chen et al. (1994) Circulation 89, 1922–1928.
Cima et al. (1991) Biotechnol. and Bioendg. 38, 145–158.
Cima and Langer (1993) Chem. Eng. Prog., 46–53.
Connolly et al. (1988) Trans. ASAIO 34, 1043–1046.
D'Amore and Smith (1993) Growth Factors, 8, 61–75.
Edelman et al. (1991) Biomaterials 12, 619–626.
Freed et al. (1993) Jour. Cell. Biochem. 51, 257–264.
Freed et al. (1994a) Jour. Biomed. Mat. Res. 28, 891–899.
Freed et al. (1994b) Bio/Technology 12, 689–693.
Gilbert et al. (1993) Transplantation 56(2), 423–427.
Gilding and Reed (1979) Polymer 20, 1459–1464.
Greisler et al. (1988) Circulation 78 (suppl I), I6–I12 (1988).
Langer and Vacanti (1993) Science 260, pp. 920–926.
Massia and Hubbell (1990) Ann. N.Y. Acad. Sci. 589, 261–270.
Mooney et al. (1992) Mat. Res. Soc. Symp. Proc. 252, 345–352.
Mooney et al. (1994) Cell Transplantation, 3(20), 203–210.
Mooney et al. (1994) Transplantation Proc. 26(6), 3425–3426.
Rogelj et al. (1989) Jour. Cell Biol. 109, 823–831.
Shayani et al. (1994) Jour. Surg. Res. 57, 495–504.
Takeda et al. (1995) Transplantation Proc. 27(1), 635–636.
Vacanti et al. (1994) Transplantation Proc. 26(6), 3434–3435.
Weinberg and Bell (1986) Science 231, 397–400.
Wintermantel et al. (1991) ASAIO Trans. 37, M334–M336.

What is claimed is:

1. A muscular, tubular tissue-engineered construct comprising:

a substantially tubular construct of living mammalian tissue having a first end and a second end, an inner surface and an outer surface;

wherein the first end, the second end, and the inner surface of the construct define a lumen passing through the construct; and wherein tissue between said inner surface and said outer surface defines a wall of mammalian smooth muscle cells;

wherein said wall comprises said mammalian smooth muscle cells oriented circumferentially about said lumen; and wherein said mammalian smooth muscle cells in said wall have a cell density of at least $10^7$ cells/cc.

2. A muscular, tubular tissue-engineered construct as in claim 1 wherein said tubular construct is capable of withstanding an internal pressure of at least 100 mm Hg for a sustained period without rupturing.

3. A muscular, tubular tissue-engineered construct as in claim 1 wherein said tubular construct is capable of withstanding an internal shear force of at least 5 dynes/cm$^2$ for a sustained period without rupturing.

4. A muscular, tubular tissue-engineered construct as in claim 1 wherein said wall further comprises a biocompatible synthetic polymeric material.

5. A muscular, tubular tissue-engineered construct as in claim 1 wherein said outer surface is substantially free of an adventitia.

6. A muscular, tubular tissue-engineered construct as in claim 1 wherein said wall is substantially free of an intermediate layer of an intima.

7. A muscular, tubular tissue-engineered construct as in claim 1 wherein said wall is substantially free of an internal elastic lamina of an intima.

8. A muscular, tubular tissue-engineered construct as in claim 1 wherein said wall is substantially free of fibroblasts in an intimal layer.

9. A muscular, tubular tissue-engineered construct as in claim 1 wherein said wall is substantially free of fibroblasts in a medial layer.

* * * * *